(12) United States Patent
Okamoto

(10) Patent No.: US 7,642,086 B2
(45) Date of Patent: Jan. 5, 2010

(54) LABELED PROBE BOUND OBJECT, METHOD FOR PRODUCING THE SAME AND METHOD FOR USING THE SAME

(75) Inventor: Tadashi Okamoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/499,711

(22) Filed: Aug. 7, 2006

(65) Prior Publication Data

US 2007/0092897 A1 Apr. 26, 2007

(30) Foreign Application Priority Data

Aug. 9, 2005 (JP) ............................. 2005-230597
Aug. 9, 2005 (JP) ............................. 2005-230598

(51) Int. Cl.
*C12M 3/00* (2006.01)
(52) U.S. Cl. .................................................. 435/287.2
(58) Field of Classification Search ........................ None
See application file for complete search history.

(56) References Cited

U.S. PATENT DOCUMENTS

| | | | |
|---|---|---|---|
| 4,747,685 A | 5/1988 | Suzuki ........................ 356/36 |
| 5,498,551 A | 3/1996 | de Jaeger et al. ............ 436/533 |
| 5,512,446 A | 4/1996 | Miyazaki et al. ............. 435/7.2 |
| 5,534,441 A | 7/1996 | Miyazaki et al. ............. 436/517 |
| 5,545,521 A | 8/1996 | Okamoto et al. ............... 435/5 |
| 5,624,798 A | 4/1997 | Yamamoto et al. ............. 435/6 |
| 5,670,315 A | 9/1997 | Yamamoto et al. ............. 435/6 |
| 5,679,516 A | 10/1997 | Okamoto et al. ............... 435/6 |
| 5,679,581 A | 10/1997 | Miyazaki et al. ............. 436/517 |
| 5,700,647 A | 12/1997 | Miyazaki et al. ............... 435/6 |
| 5,705,346 A | 1/1998 | Okamoto et al. ............... 435/6 |
| 5,744,305 A | 4/1998 | Fodor et al. .................... 435/6 |
| 5,846,730 A | 12/1998 | Miyazaki et al. ............... 435/6 |
| 5,893,999 A | 4/1999 | Tamatani et al. ........... 252/301.4 |
| 5,939,256 A | 8/1999 | Yamamoto et al. ............. 435/6 |
| 5,981,297 A * | 11/1999 | Baselt ........................ 436/514 |
| 6,004,744 A | 12/1999 | Goelet et al. ................... 435/5 |
| 6,022,961 A | 2/2000 | Yamamoto et al. ......... 536/24.3 |
| 6,024,909 A | 2/2000 | Yoshida et al. .............. 264/430 |
| 6,156,506 A | 12/2000 | Yamamoto et al. ............. 435/6 |
| 6,197,557 B1 * | 3/2001 | Makarov et al. ........... 435/91.2 |
| 6,297,008 B1 | 10/2001 | Okamoto et al. ............... 435/6 |
| 6,424,418 B2 | 7/2002 | Kawabata et al. ........... 356/445 |
| 6,440,667 B1 | 8/2002 | Fodor et al. .................... 435/6 |
| 6,500,622 B2 | 12/2002 | Bruchez, Jr. et al. ........... 435/6 |
| 6,569,671 B1 | 5/2003 | Okamoto et al. ......... 435/285.1 |
| 6,602,671 B1 | 8/2003 | Bawendi et al. .............. 435/7.1 |
| 6,737,238 B2 | 5/2004 | Suzuki et al. ................... 435/6 |
| 6,852,524 B2 | 2/2005 | Okamura et al. ......... 435/287.1 |
| 6,960,432 B2 | 11/2005 | Okamoto et al. ............... 435/6 |
| 6,963,397 B2 | 11/2005 | Suzuki et al. ................ 356/317 |
| 7,238,795 B2 * | 7/2007 | Seela et al. ................. 536/23.1 |
| 2002/0115072 A1 | 8/2002 | Okamoto et al. ............... 435/6 |
| 2002/0168648 A1 | 11/2002 | Yamamoto et al. ............. 435/6 |
| 2004/0018552 A1 | 1/2004 | Okamoto et al. ............... 435/6 |
| 2004/0132080 A1 | 7/2004 | Kawaguchi et al. ............ 435/6 |
| 2005/0158738 A1 | 7/2005 | Okamura et al. ............... 435/6 |
| 2005/0202501 A1 | 9/2005 | Yamamoto et al. ............. 435/6 |
| 2006/0029959 A1 | 2/2006 | Okamoto et al. ............... 435/6 |
| 2006/0183235 A1 | 8/2006 | Hashimoto et al. ............ 436/86 |
| 2007/0003958 A1 | 1/2007 | Okamoto et al. ............... 435/6 |

FOREIGN PATENT DOCUMENTS

| | | |
|---|---|---|
| EP | 0 304 845 | 3/1989 |
| EP | 0 392 546 | 10/1990 |
| JP | 61-225656 | 10/1986 |
| JP | 62-81566 | 4/1987 |
| JP | 62-195556 | 8/1987 |
| JP | 64-51322 | 2/1989 |
| JP | 1-95800 | 4/1989 |
| JP | 2-299598 | 12/1990 |
| JP | 7-53271 | 2/1995 |
| JP | 7-83927 | 3/1995 |
| JP | 2001-299346 | 10/2001 |
| JP | 2002-128523 | 5/2002 |

OTHER PUBLICATIONS

David R. Walt, "Bead-based Fiber-Optic Arrays", Science, vol. 287, Jan. 21, 2000, pp. 451-452.
Tadashi Okamoto, et al., "Microarray fabrication with covalent attachment of DNA using Bubble Jet technology", Nature Biotechnology, vol. 18, Apr. 2000, pp. 438-441.

* cited by examiner

*Primary Examiner*—Ann Y Lam
(74) *Attorney, Agent, or Firm*—Fitzpatrick, Cella, Harper & Scinto

(57) ABSTRACT

A method for labeling an object, which is effective when multiple types of labels are given as necessary even to a very small object such as a fine particulate substrate for use in fixation of biological substances such as probe molecules or nucleic acid primers that are used for a bioassay is provided. Further, an object given the labels is provided. Multiple types of labels can be given as necessary even to very small objects by using materials for labeling prepared in accordance with the composition condition of contained atoms corresponding to at least binary system n-digit numerical value information using a plurality of types (n types) of atoms selected beforehand as part of materials constituting the object, and presence/absence of the selected individual atoms contained or the level of the contents thereof. Further, the bioassay can be performed by the object labeled by the labeling method.

10 Claims, No Drawings

SEQUENCE LISTING

<160> NUMBER OF SEQ ID NOS: 21

<210> SEQ ID NO 1
<211> LENGTH: 18
<212> TYPE: DNA
<213> ORGANISM: Artificial
<220> FEATURE:
<223> OTHER INFORMATION: Synthesized DNA probe

<400> SEQUENCE: 1
actggccgtc gttttaca                                                 18

<210> SEQ ID NO 2
<211> LENGTH: 25
<212> TYPE: DNA
<213> ORGANISM: Artificial
<220> FEATURE:
<223> OTHER INFORMATION: Synthesized DNA probe

<400> SEQUENCE: 2
cgtacgatcg atgtagctag catgc                                         25

<210> SEQ ID NO 3
<211> LENGTH: 18
<212> TYPE: DNA
<213> ORGANISM: Artificial
<220> FEATURE:
<223> OTHER INFORMATION: Synthesized target DNA having a complimentary
      nucleotide sequence to SEQ ID NO:1

<400> SEQUENCE: 3
tgtaaaacga cggccagt                                                 18

<210> SEQ ID NO 4
<211> LENGTH: 25
<212> TYPE: DNA
<213> ORGANISM: Artificial
<220> FEATURE:
<223> OTHER INFORMATION: Synthesized target DNA having a complimentary
      nucleotide sequence to SEQ ID NO:2

<400> SEQUENCE: 4
gcatgctagc tacatcgatc gtacg                                         25

<210> SEQ ID NO 5
<211> LENGTH: 30

```
<212> TYPE: DNA
<213> ORGANISM: Artificial
<220> FEATURE:
<223> OTHER INFORMATION: Synthesized DNA probe

<400> SEQUENCE: 5
tttttttttt tttttttttt tttttttttt                                30

<210> SEQ ID NO 6
<211> LENGTH: 30
<212> TYPE: DNA
<213> ORGANISM: Artificial
<220> FEATURE:
<223> OTHER INFORMATION: Synthesized target DNA

<400> SEQUENCE: 6
aaaaaaaaaa aaaaaaaaaa aaaaaaaaaa                                30

<210> SEQ ID NO 7
<211> LENGTH: 18
<212> TYPE: DNA
<213> ORGANISM: Artificial
<220> FEATURE:
<223> OTHER INFORMATION: Synthesized DNA probe

<400> SEQUENCE: 7
gatgggcctc cggttcat                                             18

<210> SEQ ID NO 8
<211> LENGTH: 18
<212> TYPE: DNA
<213> ORGANISM: Artificial
<220> FEATURE:
<223> OTHER INFORMATION: Synthesized DNA probe

<400> SEQUENCE: 8
gatgggccac cggttcat                                             18

<210> SEQ ID NO 9
<211> LENGTH: 18
<212> TYPE: DNA
<213> ORGANISM: Artificial
<220> FEATURE:
<223> OTHER INFORMATION: Synthesized DNA probe

<400> SEQUENCE: 9
gatcggccac cggatcat                                             18

<210> SEQ ID NO 10
<211> LENGTH: 20
<212> TYPE: DNA
<213> ORGANISM: Artificial
<220> FEATURE:
<223> OTHER INFORMATION: Synthesized DNA for sense primer

<400> SEQUENCE: 10
actggcctca tcttgggcct                                           20

<210> SEQ ID NO 11
<211> LENGTH: 20
<212> TYPE: DNA
<213> ORGANISM: Artificial
<220> FEATURE:
<223> OTHER INFORMATION: Synthesized DNA for anti-sense primer

<400> SEQUENCE: 11
```

```
tgtgcagggt ggcaagtggc                                              20

<210> SEQ ID NO 12
<211> LENGTH: 20
<212> TYPE: DNA
<213> ORGANISM: Artificial
<220> FEATURE:
<223> OTHER INFORMATION: Synthesized DNA for sense primer labeled by
      replacing A with bromo-substituted A

<400> SEQUENCE: 12
actggcctca tcttgggcct                                              20

<210> SEQ ID NO 13
<211> LENGTH: 18
<212> TYPE: DNA
<213> ORGANISM: Artificial
<220> FEATURE:
<223> OTHER INFORMATION: Synthesized DNA primer

<400> SEQUENCE: 13
tgtaaaacga cggccagt                                                18

<210> SEQ ID NO 14
<211> LENGTH: 18
<212> TYPE: DNA
<213> ORGANISM: Artificial
<220> FEATURE:
<223> OTHER INFORMATION: Synthesized DNA primer

<400> SEQUENCE: 14
tgtaaaacga cggccaga                                                18

<210> SEQ ID NO 15
<211> LENGTH: 17
<212> TYPE: DNA
<213> ORGANISM: Artificial
<220> FEATURE:
<223> OTHER INFORMATION: Synthesized DNA primer

<400> SEQUENCE: 15
tgtaaaacga cggccag                                                 17

<210> SEQ ID NO 16
<211> LENGTH: 17
<212> TYPE: DNA
<213> ORGANISM: Artificial
<220> FEATURE:
<223> OTHER INFORMATION: Synthesized DNA primer

<400> SEQUENCE: 16
tgtaaaacga cggccac                                                 17

<210> SEQ ID NO 17
<211> LENGTH: 30
<212> TYPE: DNA
<213> ORGANISM: Artificial
<220> FEATURE:
<223> OTHER INFORMATION: Synthesized DNA primer

<400> SEQUENCE: 17
tttttttttt tttttttttt tttttttttt                                   30

<210> SEQ ID NO 18
<211> LENGTH: 17
<212> TYPE: DNA
```

-continued

```
<213> ORGANISM: Artificial
<220> FEATURE:
<223> OTHER INFORMATION: Synthesized DNA primer

<400> SEQUENCE: 18
gatgggcctc cggttca                                                    17

<210> SEQ ID NO 19
<211> LENGTH: 17
<212> TYPE: DNA
<213> ORGANISM: Artificial
<220> FEATURE:
<223> OTHER INFORMATION: Synthesized DNA primer

<400> SEQUENCE: 19
gatgggcctc cggttct                                                    17

<210> SEQ ID NO 20
<211> LENGTH: 20
<212> TYPE: DNA
<213> ORGANISM: Artificial
<220> FEATURE:
<223> OTHER INFORMATION: Synthesized DNA sense primer E7S

<400> SEQUENCE: 20
actggcctca tcttgggcct                                                 20

<210> SEQ ID NO 21
<211> LENGTH: 20
<212> TYPE: DNA
<213> ORGANISM: Artificial
<220> FEATURE:
<223> OTHER INFORMATION: Synthesized DNA anti-sense primer E7A

<400> SEQUENCE: 21
tgtgcagggt ggcaagtggc                                                 20
```

LABELED PROBE BOUND OBJECT, METHOD FOR PRODUCING THE SAME AND METHOD FOR USING THE SAME

BACKGROUND OF THE INVENTION

1. Field of the Invention

The present invention relates to an biological substance bound object given a label for identification for discriminating the type of each of a plurality of objects to which biological substances are individually bound, specifically the type of each of these biological substances, and a method for producing the same.

The present invention further relates to a method for discriminating a probe possessed by the object, a method for detecting, identifying and quantitatively measuring a probe bound to the object, and a method for detecting, identifying and quantitatively measuring a target substance bound to the probe.

Further, the present invention relates to a nucleic acid primer bound object given a label for identification for discriminating the type of each of a plurality of objects to which a plurality of types of nucleic acid primers are individually bound, specifically the type of each of the nucleic acid primers bound on the objects, and a method for producing the same, and a method for discriminating the type of the object, specifically the type of nucleic acid primer bound on the object. Further, the present invention relates to a method for using such a nucleic acid primer bound object given a label for identification to identify and detect or quantitatively measure the type of nucleic acid primer bound to the object, or a method for using a nucleic acid primer bound to the object to detect a single nucleotide polymorphism of a target nucleic acid.

2. Description of the Related Art

When a plurality of types of objects are treated, it is required to accurately discriminate the type of each of the objects in many cases. Particularly, if a plurality of types of objects to be treated cannot easily be discriminated by appearances, a label for identification corresponding to the type of each of objects is given to help discriminate the type of each of the objects.

For labeling for identification, there are various kinds of methods, but in essence, discriminable coded identifiers (codes), the number of which is equal to or greater than the number of types, to be discriminated, are assigned to individual types. If the object size of a target to which a label is give is large, character string type identifiers are used, in many cases, as discriminable coded identifiers (codes) used. For example, barcodes correspond to identifiers which are matched with character string type identifiers and converted into information of line widths and intervals of bars in accordance with a predetermined rule. Fundamentally, many of character string type identifiers employ a form in which a plurality of hierarchical label portions such as, for example, country codes (country numbers), area codes (toll numbers) and individual numbers in an area (in-area exchange numbers+individual line numbers) in the telephone number, are combined and integrated into one character string type identifier in order to more conveniently assign identifiers that can be expressed by a series of serial numbers.

If the object size of a target to which a label is given is small, it is technically difficult to give a visually discriminable character string type identifier described above. For example, an IC tag employs a method in which as a character string type identifier, information electronically described on an IC chip is identified via a digitized electromagnetic wave between the IC tag and an external detector. The size of this IC tag itself is in the order of 100 μm, and giving a character string type identifier to an object size of a dozen or so μm or less, and several μm or less in some cases is more technically difficult challenge.

For instance, one example of the case where the object size is a dozen or so μm or less and several μm or less in some cases is an object having probe molecules fixed on the surfaces of microscopic particles, which is used for detection of an biological substance.

For example, methods of examining a taxonomic near relative relationship by evaluating cross reactivity of antibody molecules specific to analogous microorganisms to an antigen on the surface of a target microorganism when classifying various kinds of microorganisms have been used since long ago. At this time, antibody molecules for use as a probe are fixed on the surfaces of gold fine particles, and integration of gold fine particles on the periphery of microorganisms are observed to determine presence/absence of a cross reaction. As a method for identifying an epitope sequence identified by various kinds of antibody molecules, a method in which for example, colibacillus strains expressing peptides undergoing an antigen/antibody reaction with antibody molecules fixed on the surfaces of microscopic ferrite particles are separated from random peptide library displayed by colibacillus bacteria by applying a panning method is widely known. In this method, only colibacillus strains expressing peptides having amino acid sequences capable of reacting with antibody molecules are separated in the form of being coupled to ferrite particles when magnetically microscopic ferrite particles are collected.

A main advantage possessed by microscopic particles fixing probe molecules, which are used for detection of an biological substance, is that by using means for separating microscopic particles as a solid matter from a liquid phase, a detection target substance bound by probe molecules and other contaminants existing in the liquid phase can easily be separated. Specifically, after a detection target substance existing in the liquid phase is bound to probe molecules, a conjugate of the detection target substance and probe molecules and unreacted probe molecules are temporarily separated and collected from the liquid phase by using microscopic particles fixing the probe molecules. Thereafter, whether a conjugate of the detection target substance and probe molecules actually exists in a collected mixture of the detection target substance and probe molecules and unreacted probe molecules is determined, and further, the amount of existing conjugate is quantitatively measured.

The advantage that separation from the liquid phase is facilitated by fixing probe molecules on the surface of a solid phase is also achieved by fixing probe molecules on the surface of a solid phase substrate having a macroscopic size. For example, when detecting presence/absence of a specific IgG antibody existing in a specimen sample, an antigen peptide having an epitope sequence to an Ig antibody as a detection target is fixed in a predetermined density on the surface of a solid phase substrate, the specimen sample is brought into contact with the surface of the solid phase substrate, and the IgG antibody as a detection target is fixed on the surface of the solid phase substrate through a reaction with the antigen peptide. Thereafter, the specimen sample is removed to the surface of the solid phase substrate, and an anti IgG antibody given a label for detection is then quantitatively reacted with an Fc region (stationary region) of IgG antibody molecules fixed on the surface of the solid phase substrate. The unreacted "anti IgG antibody given a label" is washed out from the surface of the solid phase substrate, and the anti IgG antibody given a label, which quantitatively reacts with the IgG antibody molecules fixed on the surface of the solid phase substrate, is detected using the label for detection, and quantitatively measured.

In the method of fixing probe molecules on the surface of the solid phase substrate having a macroscopic size, different types of probe molecules can be fixed on regions after sectioning the same substrate surface into a plurality of regions because the solid phase substrate itself is large. Specifically, when sectioning the substrate surface into a plurality of regions, individual sections are arranged in the form of an array or a matrix, and addresses for identifying the sections are then given (lot numbers are given), whereby the form of a probe array with different types of probe molecules fixed on individual sections can be provided. For example, there are forms of: a DNA probe array fixing a plurality of types of DNA nucleic acid probes, which is used for fixation of target nucleic acid molecules including a base sequence portion complementary to a base sequence of a nucleic acid probe, by a hybridization reaction with a nucleic acid probe; a peptide antigen array fixing a plurality of types of antigen peptides having known amino acid sequences, which is used for fixation of target antibody molecules having specificity to antigen peptides, by an antigen/antibody reaction; an antibody array fixing a plurality of types of known specific antibody molecules, which is used for fixation of target antigen molecules using a specific antibody, by an antigen/antibody reaction conversely; and a receptor protein array fixing a plurality of types of known receptor molecules, which is used for fixation of target base molecules to a receptor protein, by the binding of base molecules on the receptor protein.

The probe array is used when a plurality of types of target molecules contained in a specimen sample are fixed at a time using a plurality of types of corresponding probe molecules. Since the solid phase substrate used has a macroscopic size, separation from the liquid phase and subsequent washing operations are extremely easy. When detecting a target substance fixed on the substrate as a conjugate with each probe molecule on the probe array, the fixed position (address) of each probe molecule is determined beforehand, and each target substance is detected in accordance with the address.

The probe array fixing probe molecules on a solid phase substrate surface having a macroscopic size has an advantage that it is easily treated when carrying out separation from the liquid phase and detection of a target substance, and is used in a variety of fields. However, there is a fundamental disadvantage that the reaction yield is relatively low (the apparent reaction rate is low) due to a reaction between probe molecules fixed on a specific region and target molecules contained in a specimen sample on the solid phase substrate surface having a macroscopic size. Specifically, probe molecules are fixed on a limited region on the solid phase substrate surface, but target molecules contained in the specimen sample are uniformly distributed over the entire liquid phase, and therefore target molecules capable of reacting with the probe molecules are limited to those existing within a limited region and on an area adjacent to the solid phase substrate surface. When the target molecules existing within this limited region form a conjugate with fixed probe molecules, the concentration of "free target molecules" existing in the liquid phase within the region abruptly decreases, and resultantly, the reaction rate relatively decreases. As a result, the total number of target molecules forming a conjugate with probe molecules per the total number of fixed probe molecules (reaction yield) is limited. The disadvantage that the reaction yield is relatively low (the apparent reaction rate is low) becomes more noticeable as the ratio of the area of a fixing region of each probe molecule on the solid phase substrate surface decreases. In other words, this disadvantage becomes more noticeable as the number of types of probe molecules constituting the probe array increases.

Ideally, this disadvantage is eliminated by quickly stirring a reaction solution to uniformalize the distribution of concentrations in the liquid phase, but in reality, there are not a few cases where the reaction, is accomplished in a situation in which the reaction solution is gently stirred or almost left stationary when a solid phase substrate surface having a macroscopic size is used. Even if the reaction yield is relatively low (the apparent reaction rate is low), the total number of target molecules forming a conjugate with probe molecules per the total number of fixed probe molecules (reaction yield) reflects the original concentration of target molecules in the specimen solution. However, as the ratio of the area of a fixing region of each probe molecule decreases, the relationship between the total number of target molecules forming a conjugate with probe molecules (reaction yield) and the original concentration of target molecules in the specimen solution becomes harder to show a high linearity. Specifically, when a dense probe array fixing multiple types of probe molecules in the form of a dense matrix on the solid phase substrate surface having a macroscopic size is used, it becomes one of factors of reducing the quantitative accuracy when the concentration of target molecules in the specimen solution is quantitatively measured by quantitatively measurement of target molecules fixed as a conjugate with the probe molecules.

In addition, when constituting a probe array grating-like frame regions for division into sections may be provided on the periphery of fixing regions of probe molecules. Alternatively, even if the grating-like frame regions are not provided, there may be non-fixing regions of, probe molecules on the periphery of fixing regions of probe molecules. There are not a few cases where various target molecules are nonselectively adsorbed because the solid phase substrate surface is exposed on, the grating-like frame regions or the non-fixing regions of probe molecules. The nonselectively adsorbed target molecules raise a signal level of a background at the time of detection, thus causing a systematic error when a difference between a signal level detected in fixing regions of probe molecules and a signal level of a background is determined to be a signal resulting from target molecules forming a conjugate with probe molecules. In addition, they become one of factors of reducing the quantitative accuracy over an area where the concentration of target molecules in the specimen solution is low, since the reaction yield is relatively low (the apparent reaction rate is low).

A spotting method in which probe molecules prepared separately beforehand are coated and fixed on predetermined fixing regions when a probe array is prepared is widely used. In this spotting method, the density of probe molecules fixed per unit surface area has a high reproducibility as in the case where microscopic particles are put in a liquid containing probe molecules prepared separately beforehand and probe molecules are fixed on their surfaces. There is a method in which oligonucleotides synthesized sequentially on a solid phase substrate surface having a macroscopic size in accordance with the base sequence of each DNA probe (oligonucleotide) using a photolithography method is used as fixed probe molecules when DNA probe (oligonucleotide) molecules capable of being synthesized by a solid phase reaction are fixed in the form of an array. For oligonucleotides that are synthesized on the solid phase substrate surface immediately thereafter, it is difficult to observe the base sequence after synthesis, and oligonucleotides lacking bases in part may be present. Otherwise, all (oligo) nucleotides lacking one nucleotide in principle coexist in a certain ratio. Presence of such DNA molecules having base sequences different from desired ones is a factor of relatively reducing the reaction yield in a probe hybridization reaction. In some cases, if DNA molecules having base sequences different from desired ones happen to have base sequences in common with DNA probe molecules fixed on another address, different types of nucleic acid molecules different from original target nucleic acid molecules ate bound on such an address. Thus, presence of the above undesired oligonucleotides becomes one of factors of reducing the quantitative accuracy.

Probe molecule fixing fine particles with probe molecules fixed on the surfaces of microscopic particles are prepared by a method in which microscopic particles are put in a liquid containing probe molecules prepared separately beforehand to fix probe molecules on their surfaces, and therefore a phenomenon in which various target molecules are nonselectively adsorbed to the surfaces of microscopic particles is substantially, inhibited. Probe molecules to be fixed are prepared separately, and then sufficiently purified. As described later, the solid phase sequential synthesis on the surfaces of microscopic particles can avoid the disadvantages of the photolithography method described above, and therefore this method can also be suitably used.

Normally, probe molecule fixing fine particles can be kept in a state of being uniformly dispersed in a liquid phase, and from a microscopic viewpoint, a reaction between the solid phase and the liquid phase occurs with target molecules uniformly distributed over the entire liquid phase, but from a macroscopic viewpoint a uniform reaction can be carried out over the entire liquid phase. Thus, the disadvantage of a relative low reaction yield (low apparent reaction rate) which is noticeable when using a dense probe array fixing multiple types of probe molecules in the form of a dense matrix on the solid phase substrate surface with a macroscopic size is substantially eliminated if the probe molecule fixing fine particles are used. Thus, if probe molecule fixing fine particles are used, most of factors of reducing the quantitative accuracy listed in the probe array can be avoided when the concentration of target molecules in the specimen solution is quantitatively measured by quantitatively measurement of target molecules fixed as a conjugate with probe molecules.

Probe molecule fixing fine particles retains the advantage that normally, they can easily be separated from the liquid phase after completion of a reaction in a state of being uniformly dispersed in the liquid phase. For example, a solid-liquid separation method applying a filtration or centrifugal separation method can be used, and when particles themselves have a magnetic material as a main component, they can be separated from the liquid phase using a magnetic force.

Of course, probe molecule fixing fine particles fix one type of probe molecule on the surface of each microscopic particle, and therefore if multiple types of probe molecules are used, it is necessary to prepare multiple types of corresponding probe molecule fixing fine particles beforehand. These multiple types of probe molecule fixing fine particles have different probe molecules constituting individual probe molecule fixing fine particles, but they cannot easily be discriminated by appearances. In other words, it is necessary that for multiple types of probe molecule fixing fine particles, microscopic particles used be made mutually discriminable and individual probe molecule fixing fine particles be identified. Specifically, it is necessary to give labels for mutual identification to microscopic particles used.

Regarding the method in which labels for mutual identification are given to microscopic particles constituting probe molecule fixing fine particles, some proposals have been made. For example, Japanese Patent Application Laid-Open No. S61-225656 describes a method of identification by a difference in particle diameter of microscopic particles used; Japanese Patent Application Laid-open No. S62-081566 describes a method of performing discrimination using a difference in particle diameter of microscopic particles and fluorescent labels (n types in total) in combination; Japanese Patent Application Laid-Open No. S62-195556 describes a method of performing discrimination by coloring microscopic particles; Japanese Patent Application Laid-Open No. H01-095800 describes a method of performing discrimination by forming microscopic particles with different metal elements; Japanese Patent Application Laid-Open No. H02-299598 describes a method of performing discrimination by staining; Japanese Patent Application Laid-Open No. H07-083927 describes a method of using microscopic particles as inorganic fluorescent materials and performing discrimination by fluorescent wavelengths thereof; U.S. Pat. No. 6,602,671 describes a method of performing discrimination using semiconductor nanocrystals for microscopic particles; U.S. Pat. No. 6,440,667 describes a method of performing discrimination using microscopic particles having different magnetizations, colors and shapes; and U.S. Pat. No. 6,500,622 describes a method of performing discrimination using semiconductor nanofluorescent particles for microscopic particles. They relate to techniques for giving lot numbers (labels) to particles individually.

In these conventional techniques, the number of types of discriminable microscopic particles, specifically the number of types of labels is a dozen or so at most, and the methods are poor in extensibility when the number of types of labels is further increased. Particularly when the number of types of labels is further increased while commonness for the particle diameter, the shape and the main component material of microscopic particles is maintained, the methods are poor in extensibility.

As described above, when for various kinds of biological substances contained in the liquid phase, for example nucleic acid molecules, proteins, sugar chain molecules and the like, the presence/absence of these substances is determined or their contents are measured, a method in which a substance (usually referred to as probe molecules) uniquely bound to an examination object substance (target substance) is made to act on the substance to form a conjugate on a temporary basis and the conjugate is separated from the liquid phase is widely used. Specifically, a method in which probe molecules are fixed on the solid phase surface, whereupon a conjugate is formed with a target substance existing in the liquid phase, and the solid phase and the liquid phase are separated is widely used. After separation from the liquid phase, detection means for adapting the presence/absence of a target substance forming a conjugate with probe molecules and the amount thereof is used.

In recent years a technique of carrying out a PCR (Polymerase Chain Reaction) reaction and a one nucleotide elongation reaction using a terminator nucleotide in conjunction on a solid phase using as a primer a nucleic acid fixed on the solid phase surface has been developed. Japanese Patent Application Laid-Open No. 2001-299346 discloses one method of so called a solid phase PCR in which one set of PCR primers consisting of two types of oligonucleotides is fixed on one matrix of a nucleic acid array to carry out a plurality of PCRs on one solid phase. U.S. Pat. No. 6,004,744 describes one nucleotide elongation using nucleic acid primers fixed on the solid phase.

At this time, as compared to a probe array regularly fixing a plurality of types of probe molecules on a solid phase substrate having a large surface area, probe molecule fixing, fine particles individually fixing probe molecules on the surfaces of fine particles are significantly excellent in reactivity with a target substance in the liquid phase and quantitativeness thereof. However, in the probe array, the type of each probe molecule can easily be identified based on its fixation position (address), but in probe molecule fixing fine particles, it is necessary to give labels to fine particles for use in fixation beforehand and identify the labels to identify the types of probe molecules.

SUMMARY OF THE INVENTION

For means for giving labels to fine particles, several types have been proposed as described above, but applicable types are limited, and if the number of types of probe molecules used is large, the purpose of giving labels to all types of probe molecules cannot be satisfied. Particularly, a labeling method excellent in extensibility, which is capable of increasing the number of types of labels as necessary while maintaining the commonness for the size, the shape and the main component material as in fine particles for use in fixation of probe molecules, is desired.

The present invention solves the aforementioned problems, and an object of the present invention is to provide a labeling method excellent in extensibility, which makes it possible to increase the number of types of available labels as necessary while objects to be given labels are made to have a very small size and have a common shape and main component material, an biological substance bound object labeled by the labeling method, a method for discriminating the biological substance bound object and an biological substance bound to the biological substance bound object, a method for detecting, identifying and quantitatively measuring the biological substance and a method for detecting, identifying and quantitatively measuring a target substance bound to the biological substance.

As a result of conducting vigorous studies for solving the aforementioned problems, the present inventor has first conceived the following. For example, for the size of microscopic particles for use in fixation of probe molecules, the particle diameter is selected to be several μm or less and in the submicron range in some cases, since the microscopic particles are uniformly dispersed in the liquid phase. At this time, for uniforming the amounts of probe molecules fixed on the surfaces of microscopic particles, it is necessary to make uniform the particle diameters of fine particles used to make uniform the surfaced areas of individual fine particles. Of course, it is necessary to make the outer shapes of fine particles equally spherical. Further, if the materials of the surfaces of fine particles are utterly different when probe molecules prepared separately are fixed on the surfaces of the fine particles, it is necessary to use different fixing means accordingly. Specifically, in the case of metallic fine particles, it is necessary to use different fixing means if metal elements constituting the fine particles are utterly different. Conversely, if means for fixing probe molecules on the surface are different, it is difficult to equalize the densities of probe molecules fixed per unit area.

Thus, a labeling method excellent in extensibility, which is capable of increasing the number of types of labels as necessary while maintaining the commonness for the particle diameter, the shape and the main component material of microscopic particles, is desirable. The present inventor has developed a labeling method having high extensibility, which meets the requirement of maintaining the commonness for the particle diameter, the shape and the main component material, has no ambiguity in identification of given labels, and can arbitrarily increase and decrease the number of types of labels that can be given as necessary. As a result, it has been found that for example, a material which can have a collateral component capable of being added arbitrarily as a component capable of being blended in a small amount in addition to a main component can be selected as a material which is used when preparing microscopic particles, and the composition of the collateral component capable of being added arbitrarily can be used to add information. Specifically, it has been conceived that if as the composition of such a collateral component capable of being added arbitrarily, a plurality of types of atoms are selected beforehand, and for these (n) types of atoms, the presence/absence of individual atoms contained is selected, a state of two levels is provided for each atom, and the composition condition, of contained atoms corresponding to binary system n-digit numerical value information can be set using the number (n) of types of atoms selected beforehand and the presence/absence of the selected individual atoms contained. Further, it has been conceived that for generalizing this method, if a plurality of types of atoms are selected beforehand, and for these (n) types of atoms, a plurality of levels, e.g. M levels for the content are set for each atom, a state of M levels is provided for each atom, and the composition condition of contained atoms corresponding to M-ary system n-digit numerical value information can be set using the number (n) of types of atoms selected beforehand and the level of contents of the selected individual atoms. In addition to these ideas, the present inventor has confirmed that for the number (n) of types of atoms selected beforehand, the presence/absence of the selected individual atoms or a difference in level of the content, for example, the level of the content can be specified for a plurality of types of atoms selected beforehand if various kinds of analysis means are applied even in the case of fine particles having a particle diameter of several μm or less, and label information given as a composition of such a collateral component can sufficiently discriminated, leading to the completion of the present invention.

In addition, in the present invention, the label includes at least two types of atoms selected from a plurality of types of atoms selected beforehand, and as means for reading the label, at least any of mass spectrometry, X-ray photoelectron spectroscopy and Auger electron spectroscopy, which are means suitable for measurement of the type of atom and the amount of existing atom, is used.

Specifically, the biological substance bound object according to the present invention is an object to which an biological substance is bound, wherein the biological substance is bound to the surface of the object, the object is given a label, the label includes at least two types of atoms selected from a plurality of types of atoms selected beforehand, and the label is identified by at least any of mass spectrometry, X-ray photoelectron spectroscopy and Auger electron spectroscopy.

The biological substance is a substance (biopolymer, etc.) originating from an organism, such as, for example, a natural or synthetic peptide, a protein, an enzyme, a saccharide, a lectin, a virus, bacteria, a nucleic acid such as DNA or RNA, or an antibody. Further, in the present invention, not only substances extracted directly from organisms, but also substances prepared by chemical treatment, chemical modification and the like of those substances, and further, synthesized substances like artificial nucleic acids are included.

The biological substance is preferably a probe or a nucleic acid primer.

At this time, a plurality of types of atoms selected beforehand are preferably selected from various kinds of atoms that are used when forming the object to which the biological substance is bound, or the surface thereof, rather than atoms constituting the biological substance. Specifically, atoms which are included in a group of atoms left after a group of atoms constituting the biological substance is excluded from a group of various kinds of atoms capable of being used when forming the object or the surface thereof and which can be detected by any of mass spectrometry, X-ray photoelectron spectroscopy and Auger electron spectroscopy can suitably be used as a plurality of types of atoms selected beforehand. The label may be identified by the detection result that any of "at least two types of atoms selected" is not detected, specifically the content of the atom is 0. In other words, in the present invention, "inclusion of at least two types of atoms selected" means the "state in which a label can be identified by noting the contents of the atoms".

One aspect of the biological substance bound object of the present invention is an object to which a probe is bound, wherein the probe is bound to the surface of the object, the object is given a label, the label gives identification information discrete identification information allowing individual objects, specifically individual probes to be discriminated for a plurality of objects as label targets, specifically a plurality of probes bound to the objects, and the composition condition of contained atoms corresponding to binary system n-digit numerical value information is formed using the number (n) of types of atoms selected beforehand and the presence/absence of the selected individual atoms contained, whereupon using a label element having a composition satisfying the composition condition of contained atoms, the discrete identification information expressed as the binary system n-digit numerical value information is given.

Another aspect of the biological substance bound object of the present invention is an object to which a probe is bound, wherein the probe is bound to the surface of the object, the object is given a label, the label gives identification information discrete identification information allowing individual objects, specifically individual probes to be discriminated for a plurality of objects as label targets, specifically a plurality of probes bound to the objects, and the composition condition of contained atoms corresponding to at least binary system n-digit numerical value information is formed using the number (n) of types of atoms selected beforehand and the level of contents of the selected individual atoms, whereupon using a label element having a composition satisfying the composition condition of contained atoms, the discrete identification information expressed as the at least binary system n-digit numerical value information is given.

Use of the method for labeling an object according to the present invention allows multiple types of labels to be given as necessary to very small objects such as, for example, fine particulate bases that are used for fixation of probe molecules for use in detection of an biological substance by using, as a part of materials forming the objects, a labeling material prepared in accordance with the composition condition of contained atoms corresponding to at least binary system n-digit numerical value information using the number (n) of types of atoms selected beforehand and the presence/absence of the selected individual atoms contained or the level of the contents thereof.

Another aspect of the biological substance bound object of the present invention is an object to which a nucleic acid primer is bound, wherein the nucleic acid primer is bound to the surface of the object, the object is given a label, the label gives discrete identification information allowing individual objects, specifically individual nucleic acid primers to be discriminated for a plurality of objects as label targets, specifically a plurality of nucleic acid primers bound to the objects, and the composition condition of contained atoms corresponding to binary system n-digit numerical value information is formed using the number (n) of types of atoms selected beforehand and the presence/absence of the selected individual atoms contained, whereupon using a label element having a composition satisfying the composition condition of contained atoms, the discrete identification information expressed as the binary system n-digit numerical value information is given.

Another aspect of the biological substance bound object of the present invention is an object to which a nucleic acid primer is bound, wherein the nucleic acid primer is bound to the surface of the object, the object is given a label, the label gives discrete identification information allowing individual objects, specifically individual nucleic acid primers to be discriminated for a plurality of objects as label targets, specifically a plurality of nucleic acid primers bound to the objects, and the composition condition of contained atoms corresponding to at least binary system n-digit numerical value information is formed using the number (n) of types of atoms selected beforehand and the level of the contents of the selected individual atoms, whereupon using a label element having a composition satisfying the composition condition of contained atoms, the discrete identification information expressed as the at least binary system n-digit numerical value information is given.

Use of the method for labeling an object according to the present invention allows multiple types of labels to be given as necessary to very small objects such as, for example, fine particulate bases that are used for fixation of nucleic acid primer molecules for use in a PCR by using, as a part of materials forming the objects, a labeling material prepared in accordance with the composition condition of contained atoms corresponding to at least binary system n-digit numerical value information using the number (n) of types of atoms selected beforehand and the presence/absence of the selected individual atoms contained or the level of the contents thereof. In the present invention, by making use of this advantage, multiple types of objects given labels are prepared, different types of nucleic acid primers are bound to the surfaces of the multiple types of objects to form objects to which nucleic acid primers are bound.

DESCRIPTION OF THE EMBODIMENTS

Preferred embodiments of the present invention will now be described in detail.

As outlined previously, in the method for labeling an object which is used in the present invention, for example, a material which can have a collateral component capable of being added arbitrarily as a component capable of being blended in a small amount in addition to a main component can be selected as a material which is used when preparing microscopic particles, and the composition of the collateral component capable of being added arbitrarily is used to add label information. Specifically, if as the composition of such a collateral component capable of being added arbitrarily, a plurality of types of atoms are selected beforehand, and for these (n) types of atoms, the presence/absence of individual atoms contained is selected, a state of two levels is provided for each atom. The composition condition of contained atoms corresponding to binary system n-digit numerical value information can be set using the number (n) of types of atoms selected beforehand and the presence/absence of the selected individual atoms contained, and label information is given by the set compositions of contained atoms. Further, for generalizing this method, if a plurality of types of atoms are selected beforehand, and for these (n) types of atoms, a plurality of levels, e.g. M levels for the content are set for each atom, a state of M levels is provided for each atom. This is used to achieve a method having extensibility, which is capable of increasing the number of types of labels as necessary by setting the composition condition of contained atoms corresponding to M-ary system n-digit numerical value information using the number (n) of types of atoms selected beforehand and the level of the contents of the selected individual atoms.

Specifically, in the method for labeling an object which is used in the present invention, a plurality of types of atoms are first selected beforehand as collateral components capable of being added arbitrarily when preparing the object, and for these (n) types of atoms, the contents ($C_i$; i=1, . . . , n) of selected individual atoms are used to set vector type information $\{C_1, \ldots, C_i, \ldots, C_n\}$ having as elements the contents ($C_i$) of these n types of atoms. This vector type information $\{C_1, \ldots, C_i, \ldots, C_n\}$ corresponds to points existing discretely on the corresponding n-dimensional space ($C_1, \ldots, C_i, \ldots, C_n$). The object is constituted by a main component and the collateral component capable of being added arbitrarily, and when the content of the main component is expressed as $C_0$, the overall composition can be expressed as vector type information $\{C_0, C_1, \ldots, C_i, \ldots, C_n\}$. In other words, the composition condition: $g(C_1, \ldots, C_i, \ldots, C_n)$ of contained atoms for achieving the overall composition: $\{C_0, C_1, \ldots, C_i, \ldots, C_n\}$ are determined by the composition $\{C_1, \ldots, C_i, \ldots, C_n\}$ of the collateral component capable of being added arbitrarily. When total number of $N_{TOTAL}$ ways is selected as the composition of the object, the composition condition: $g(C_1, \ldots, C_i, \ldots, C_n)$ of contained atoms for achieving the overall composition: $\{C_0, C_1, \ldots, C_i, \ldots, C_n\}$ is the total number of $N_{TOTAL}$ ways.

The vector type information: $\{C_0, C_1, \ldots, C_i, \ldots, C_n\}$ showing the overall composition of the total number of $N_{TOTAL}$ ways corresponds to a set of discrete points of the total number of $N_{TOTAL}$ existing in the vicinity of a point ($C_0$, 0, . . . , 0, . . . , 0) on the corresponding (n+1)-dimensional space ($C_0, C_1, \ldots, C_i, \ldots, C_n$). The composition condition: $g(C_1, \ldots, C_i, \ldots, C_n)$ of contained atoms corresponds to a function (operator) matching the vector type information: $\{C_0, C_1, \ldots, C_i, \ldots, C_n\}$ showing the overall composition with the vector type information $\{C_1, \ldots, C_i, \ldots, C_n\}$ showing the content of the collateral component capable of being added arbitrarily. Specifically, matching which can be expressed as $g(C_1, \ldots, C_i, \ldots, C_n) \rightarrow \{C_0, C_1, \ldots, C_i, \ldots, C_n\}$ can be performed. In the present invention, the detection accuracy of detection means used is considered so that compositions can be mutually discriminated by selecting appropriate detection means when the composition condition of the total number of $N_{TOTAL}$ ways is set beforehand for the content $\{C_1, \ldots, C_i, \ldots, C_n\}$ of the collateral component capable of being added arbitrarily, and then the content $\{C_1, \ldots, C_i, \ldots, C_n\}$ of the collateral component capable of being added arbitrarily is "discretely" selected.

For articles showing an overall composition of the total number of $N_{TOTAL}$ ways, in which compositions can be mutually discriminated, a set $\{f(N)\}$ of discrete numerical value information of the total number of $N_{TOTAL}$ ways: $f(N)$ is separately selected as a symbol (type number) showing a difference in type (difference in composition) between the articles. One element $f(N)$ of the set $\{f(N)\}$ of discrete numerical value information of the total number of $N_{TOTAL}$ ways: $f(N)$ is matched with each element $g(C_1, \ldots, C_i, \ldots, C_n)$ of a set $\{g(C_1, \ldots, C_i, \ldots, C_n)\}$ of the composition condition: $g(C_1, \ldots, C_i, \ldots, C_n)$ of contained atoms of the total number of $N_{TOTAL}$ ways determined by the content $\{C_1, \ldots, C_i, \ldots, C_n\}$ of the collateral component capable of being added arbitrarily, which "is discretely" selected, by "one-to-one matching" shown by $g(C_1, \ldots, C_i, \ldots, C_n) \leftrightarrow f(N)$. Specifically, the "discrete identification information" corresponding to the symbol (type number) showing a difference in type (difference in composition) between articles and expressed as the numerical value information $f(N)$ is given as a label using the composition: $\{C_1, \ldots, C_i, \ldots, C_n\}$ set "discretely".

The labeled biological substance bound object according to the present invention has been achieved by newly finding a method for "discretely" setting the composition: $\{C_1, \ldots, C_i, \ldots, C_n\}$ constituting a "label" so that the total number $N_{TOTAL}$ of types of articles showing the overall composition in which compositions can be mutually discriminated and applying the method when using a method for labeling the object.

At this time, in the present invention, the label includes at least two types of, atoms selected from a plurality of types of atoms selected beforehand, and as means for reading the label, at least any of mass spectrometry, X-ray photoelectron spectroscopy and Auger electron spectroscopy, which are means suitable for measurement of the type of atom and the amount of existing atom, is used.

The biological substance bound object of the present invention is an object to which an biological substance is bound, wherein the biological substance is bound to the surface of the object, the object is given a label, the label includes at least two types of atoms selected from a plurality of types of atoms selected beforehand, and the label is identified by at least any of mass spectrometry, X-ray photoelectron spectroscopy and Auger electron spectroscopy.

The labeled biological substance bound object according to the present embodiment described above may be, for example, an object to which an biological substance is bound, wherein the biological substance is bound to the surface of the object, the object is given a label, the label gives identification information discrete identification information allowing individual objects, specifically individual biological substances to be discriminated for a plurality of objects as label targets, specifically a plurality of biological substances bound to the objects, and a set $\{g_j(C_1, \ldots, C_i, \ldots, C_n): j=1, \ldots, N_{LABEL}\}$ of the composition condition: $g_j(C_i, \ldots, C_i, \ldots, C_n)$ of contained atoms of the number of elements of $N_{LABEL}$ (wherein $N_{LABEL}$ is an integer meeting the requirement of $1 \leq N_{LABEL} \leq N_{TOTAL}$) corresponding to a subset of a set $\{g(C_i, \ldots, C_i, \ldots, C_n)\}$ of the composition condition: $g(C_1, \ldots, C_i, \ldots, C_n)$ of contained atoms of the total number of $N_{TOTAL}$ ways is formed in accordance with the order of the setting of the composition condition capable of forming a set $\{g(C_1, \ldots, C_i, \ldots, C_n)\}$ of the composition condition: $g(C_1, \ldots, C_i, \ldots, C_n)$ of contained atoms of the total number of $N_{TOTAL}$ ways using the number (n) of types of atoms selected beforehand and the contents ($C_i$; i=1, ..., n) of the selected individual atoms, a set $\{f_j(N): j=1, \ldots, N_{LABEL}\}$ of numerical value information: $f_j(N)$ of the number of elements of $N_{LABEL}$ (wherein $N_{LABEL}$ is an integer meeting the requirement of $1 \leq N_{LABEL} \leq N_{TOTAL}$) is formed, and each element $g_j(C_1, \ldots, C_i, \ldots, C_n)$ of a set $\{g_j(C_1, \ldots, C_i, \ldots, C_n): j=1, \ldots, N_{LABEL}\}$ of the composition condition: $g_j(C_i, \ldots, C_i, \ldots, C_n)$ of contained atoms of the number of elements of $N_{LABEL}$ matched on a one-to-one basis with each element $f_j(N)$ of a set $\{f_j(N): j=1, \ldots, N_{LABEL}\}$ of numerical value information: $f_j(N)$ of the number of elements of $N_{LABEL}$ is selected, whereupon using a label element having the composition: $\{C_1, \ldots, C_i, \ldots, C_n\}$ satisfying the composition condition: $g_j(C_1, \ldots, C_i, \ldots C_n)$ of the contained atoms, the discrete identification information expressed as the numerical value information $f_j(N)$ matched on a one-to-one basis with the $g_j(C_1, \ldots, C_i, \ldots, C_n)$ ($g_j(C_1, \ldots, C_i, \ldots, C_n)$ ↔ $f_j(N)$) is given, and the total number: $N_{TOTAL}$ of elements of the set $\{g_j(C_1, \ldots, C_i, \ldots, C_n)\}$ of the composition condition: $g_j(C_1, \ldots, C_i, \ldots, C_n)$ of the contained atoms is select to meet the requirement of $N_{TOTAL} \geq 2^n - 1$, and the number of elements $N_{LABEL}$ of the set $\{f_j(N): j=1, \ldots, N_{LABEL}\}$ of the numerical value information: $f_j(N)$ and the number of elements $N_{LABEL}$ of the set $\{g_j(C_1, \ldots, C_i, \ldots, C_n): j=1, \ldots, N_{LABEL}\}$ of the composition condition: $g_j(C_1, \ldots, C_i, \ldots, C_n)$ of the contained atoms are selected to meet the requirement of $N_{TOTAL} \geq N_{LABEL} \geq n \cdot (n-1) + 1$.

Further, the biological substance bound object can be an object to which an biological substance is bound, wherein the biological substance is bound to the surface of the object, the object is given a label, the label gives identification information discrete identification information allowing individual objects, specifically individual biological substances to be discriminated for a plurality of objects as label targets, specifically a plurality of biological substances bound to the objects, and a set $\{g(C_1, \ldots, C_i, \ldots, C_n)\}$ of the composition condition: $g(C_1, \ldots, C_i, \ldots, C_n)$ of contained atoms of the total number of $N_{total}$ ways matched on a one-to-one basis with each element $f(N)$ of a set; $\{f(N)\}$ of numerical value information: $f(N)$ of the total number of, $N_{total}$ ways is formed using the number (n) of types of atoms selected beforehand and the contents ($C_i$; i=1, ..., n) of the selected individual atoms, whereupon using a label element having the composition: $\{C_1, \ldots, C_i, \ldots, C_n\}$ satisfying the composition condition: $g_j(C_1, \ldots, C_i, \ldots, C_n)$ of the contained atoms, the discrete identification information expressed as the numerical value information $f_j(N)$ matched on a one-to-one basis with the $g_j(C_1, \ldots, C_i, \ldots, C_n)$ ($g_j(C_1, \ldots, C_i, \ldots, C_n)$ ↔ $f_j(N)$) is given, and the total number: $N_{TOTAL}$ of elements of the set $\{f(N)\}$ of the numerical value information: $f(N)$ is selected to meet the requirement of $N_{TOTAL} \geq 2^n - 1$.

At this time, an embodiment of in which information corresponding to "binary system n-digit numerical value information" generated by converting the contents ($C_i$; i=1, ..., n) of individual atoms into values of two levels, particularly two levels of "presence/absence of the atom contained" for the composition: $\{C_1, \ldots, C_i, \ldots, C_n\}$ is used as $f(N)$ is the first embodiment of the present embodiment. An embodiment in which the method of the first embodiment is made more general and given extensibility such that "M-ary system n-digit numerical value information" generated by converting the contents ($C_i$; i=1, ..., n) of individual atoms into values divided into two or more levels, for example M levels is used as numerical value information: $f(N)$ is the second embodiment of the present embodiment.

The labeled biological substance bound object according to the first embodiment of the present embodiment is an object to which an biological substance is bound, wherein the biological substance is bound to the surface of the object, the object is given a label, the label gives identification information discrete identification information allowing individual objects, specifically individual biological substances to be discriminated for a plurality objects as label targets, specifically a plurality of biological substances bound to the objects, and the composition condition of contained atoms corresponding to binary system n-digit numerical, value information is formed using the number (n) of types of atoms selected beforehand and the presence/absence of the selected individual atoms contained, whereupon using a label element having a composition satisfying the composition condition of contained atoms, the discrete identification information expressed as the binary system n-digit numerical value information is given.

The labeled biological substance bound object according to the second embodiment of the present embodiment in which the first embodiment is made to have further extensibility is an object to which an biological substance is bound, wherein the biological substance is bound to the surface of the object, the object is given a label, the label gives identification information discrete identification information allowing individual objects, specifically individual biological substances to be discriminated for a plurality of objects as label targets, specifically a plurality of biological substances bound to the objects, and the composition condition of contained atoms corresponding to at least binary system n-digit, numerical value information is formed using the number (n) of types of atoms selected beforehand and the level of contents of the selected individual atoms, and whereupon using a label element having a composition satisfying the composition condition of contained atoms, the discrete identification information expressed as the at least binary system n-digit numerical value information is given.

Further, preferred embodiments thereof may include the embodiments described below.

For example, for the objects according to the first embodiment and the second embodiment of the present embodiment described above, in the label, the number (n) of types of atoms selected beforehand can be 5 or more, and the type N of numerical value information represented by the number (n) of types of the atoms and the contents of the selected individual atoms; $N \geq \Sigma nCm = 2^n - 1$ ($1 \leq m \leq n$, m and n are positive integers) can be 31 or more.

In the label, the number (n) of types of atoms selected beforehand can be 8 or more, and the type N of numerical value information represented by the number (n) of types of the atoms and the contents of the selected individual atoms; $N \geq \Sigma nCm = 2^n - 1$ ($1 \leq m \leq n$, m and n are positive integers) can be 255 or more.

As an aspect showing high extensibility, in the label, the number (n) of types of atoms selected beforehand can be 12 or more, and the type N of numerical value information represented by the number (n) of types of the atoms and the contents of the selected individual atoms; $N \geq \Sigma nCm = 2^n - 1$ ($1 \leq m \leq n$, m and n are positive integers) can be 4095 or more. Alternatively, in the label, the number (n) of types of atoms selected beforehand can be 16 or more, and the type N of numerical value information represented by the number (n) of types of the atoms and the contents of the selected individual atoms; $N \geq \Sigma nCm = 2^n - 1$ ($1 \leq m \leq n$, m and n are positive integers) can be 65535 or more.

For the labeled biological substance bound object according to the first embodiment and the second embodiment of the present embodiment described above, the shape of the object itself is not used in label information, and can arbitrarily be selected. Thus, the shape of the object can be selected from particles of indeterminate forms, particles of determinate forms, fibers and sheets.

The labeled biological substance bound object according to the present embodiment uses in a label the number (n) of types of atoms selected beforehand, the presence/absence of the selected individual atoms contained, or the level thereof, and may be applied to, for example, a magnetic material having a plurality of types of atoms as components. Thus, an aspect in which the object is a magnetic material can be selected.

In addition to the shape of the object, the size of the object is not used in label information, and therefore, in the labeled object according to the present embodiment, the size of the object can arbitrarily be selected according to its application. For example, as the size of the object, the particle diameter equivalent size can be selected to be in the range of 1 nm to 10 µm when the object is in the form of fine particles, and at least two of longitudinal, lateral and height sizes can be selected to be in the range of 1 nm to 10 µm when the object is in the form of fibers or chips. In addition, the lower limit of the size is preferably selected to be 100 nm or more when counting applying a cytometry method is used for detection.

Examples of the biological substance bound to the object according to the present embodiment include nucleic acids, DNAs, RNAs, cDNAs, cRNAs, oligodeoxyribonucleotides, polydeoxyribonucleotides, oligoribonucleotides, polyribonucleotides, peptide nucleic acids (PNAs), oligopeptide nucleic acids, peptides, oligopeptides, polypeptides, proteins, antigens, antibodies, enzymes, ligands, ligand receptors, sugars, sugar chains and the like.

The biological substance according to the present invention has a function as a probe, but preferably has a function as a nucleic acid primer.

In the present invention, an object to which a probe is bound is called a probe bound object, and an object to which a nucleic acid primer is bound is called a nucleic acid primer bound object.

The probe bound to the probe bound object according to the present invention refers to a substance having a function as so called a probe, specifically a function as one of a pair of substances capable of being bound with the substances recognizing each other. Further, the substance may be any substance as long as it has such a function and can be bound to the object according to the present invention. Examples of such substances include nucleic acids, DNAs, RNAs, cDNAs, cRNAs, oligodeoxyribonucleotides, polydeoxyribonucleotides, oligoribonucleotides, polyribonucleotides, peptide nucleic acids (PNAs), oligopeptide nucleic acids, peptides, oligopeptides, polypeptides, proteins, antigens, antibodies, enzymes, ligands, ligand receptors, sugars, sugar chains and the like.

In the labeled nucleic acid primer bound object according to the present invention, the nucleic acid primer bound to the object may be capable of performing a function as so called a nucleic acid primer, specifically at least one nucleotide elongation from the 3' terminal of the primer with a target nucleic acid as a matrix. Specifically, examples of single strand nucleic acid molecules capable of being used as a nucleic acid primer in the elongation reaction may include oligodeoxyribonucleotides, polydeoxyribonucleotides, oligoribonucleotides and polyribonucleotides.

A method for binding the biological substance to an object according to the present invention may be any method as long as it allows formation of a state in which the biological substance is bound to the object in a state in which the substance can exhibit a function as a probe or a nucleic acid primer, and for example, covalent bonding, ionic bonding and physical adsorption may be used.

When the biological substance is an oligomer or a polymer constituted by a plurality of monomers, a method in which the biological substance is synthetically bound on the object by so called solid phase sequential synthesis may be employed, since the basic configuration of the present invention is an aspect in which the biological substance is bound to the object. The solid phase sequential synthesis is a method which has been generally used in synthesis of nucleic acids, synthesis of peptide nucleic acids, synthesis of peptides and the like, and in the present invention, the method may be employed directly. In preparation of so called nucleic acid chips, for example, U.S. Pat. No. 5,744,305 specification describes a method in which a nucleic acid probe is synthetically bound on a solid phase substrate using photolithography and a deprotection reaction by light. However, this method still has problems concerning the reaction efficiency of the optical deprotection reaction or the reaction yield and the reaction rate due to the fact that the entire reaction is an uneven reaction on a substrate, and a problem of formation of a large number of undesired short strand nucleic acids on the substrate.

In the present invention, if particles, fine particles or the like are appropriately selected as an object to which the biological substance is bound, there is convenience of applicability to a solid phase automatic synthesizer for use in the synthesis of nucleic acids, synthesis of peptide nucleic acids and synthesis of peptides described above. Further, because of the solid phase synthesis, specifically because particles are used although an uneven system, a high reaction yield and a high reaction rate can be obtained as compared to a case where a heavy and long substrate is used. For a synthesis scheme, a general scheme may be used, e.g. an acid is used for deprotection of a nucleic acid, sequential reaction, and therefore the amount of unnecessary short strand nucleic acid existing is reduced as compared to a method in which optical deprotection is used on a the substrate.

When the aforementioned solid phase synthesis is used, for example, a hydroxide group can be introduced into the surface of an object to which a nucleic acid is to be bound, followed by performing automatic synthesis, if the biological substance is a nucleic acid. If the biological substance is a peptide nucleic acid or a peptide, an amino group can be introduced into the surface of an object, followed by performing automatic synthesis. For introduction of the amino group into the surface of the object, a silane coupling agent having an amino group may be used.

In addition, as a method for binding an biological substance to an object according to the present invention, a method in which an biological substance synthesized and purified beforehand is given can be employed. For the method for giving to the object an biological substance synthesized and purified beforehand, a method which has been previously used can be applied. Such a method may be, for example, a method in which an object is treated with a silane coupling agent having a various kinds of functional groups (amino group, thiol group, hydroxide group, epoxy group, succinimide ester group, maleimide group, halide group, etc.), a desired functional group is introduced into the surface of the object, and the object is then reactively bound to an biological substance having a functional group capable of reacting with the aforementioned functional group. If the functional groups do not match, a linker substance having two different functional groups, for example N-(6-maleimidecaproyloxy)succinimide (Dojindo Laboratories) may be interposed to achieve binding. The functional group on the biological substance side may be a functional group reacting with the functional group introduced into the object as described above, or a functional group reacting via the abovementioned linker substance. For example, if the biological substance is a nucleic acid, examples of the functional group may include an amino group, a thiol group and a succinimide group. If the biological substance is a peptide, a protein, an enzyme or an antibody, a thiol group may be introduced synthetically into the biological substance using a cysteine residue, or a thiol group of an existing cysteine residue may be used to form a maleimide group on the surface of the object using, for example, an amino silane coupling agent and the aforementioned N-(6-maleimidecaproyloxy)succinimide, and the maleimide group may be bound to the thiol group of the aforementioned biological substance.

Examples of ionic bonding may include ionic bonding between an amino group and a thiol group. When ionic bonding is used, it is necessary to adjust pH at the time of binding reaction to control the ionization of reacting functional groups as a matter of course.

The present invention further provides an invention of a method in which for an biological substance bound object given a label, the given label is identified to perform mutual discrimination of objects and hence mutual discrimination of biological substances bound to the objects, in addition to the method of the biological substance bound object according to the present invention having the configuration described above.

Specifically, the method for discriminating an object and an biological substance according to the present invention is a method for discriminating the type of biological substance bound object given the aforementioned label, specifically the type of an biological substance bound to the object, wherein the composition condition of contained atoms corresponding to at least binary system n-digit numerical value information using the number (n) of types of atoms selected beforehand and the presence/absence the selected individual atoms contained or the level of the contents thereof, whereupon using labels given to the individual objects using label elements having compositions satisfying the composition condition of the contained atoms, the presence/absence of individual atoms contained or the level of the contents thereof is identified for the plurality of types of atoms selected beforehand in the composition possessed by the label element using detection means for detecting the presence/absence of the atom contained or the level of the content thereof for the plurality of types of atoms selected beforehand, the composition condition of the contained atoms which is satisfied in the composition of the label element is discriminated, and corresponding at least binary system n-digit numerical value information is extracted, and the types of individual biological substance bound objects are identified based on the discrete identification information expressed as the at least binary system n-digit numerical value information.

Further, the present invention provides a method for detecting, identifying or quantitatively measuring an biological substance for an biological substance bound object given a label.

Specifically, the method for detecting, identifying or quantitatively measuring an biological substance according to the present invention is a method for detecting, identifying or quantitatively measuring an biological substance bound to an object, wherein the type of the object, specifically the type of biological substance bound to the object is discriminated by using a label of the object given using the label element, and identifying the presence/absence of individual atoms contained or the level of the contents thereof for the plurality of types of atoms selected beforehand in the composition possessed by the label element using detection means for detecting the presence/absence of the atom contained or the level of the content thereof for the plurality of types of atoms selected beforehand, discriminating the composition condition of the contained atoms which is satisfied in the composition of the label element, and extracting corresponding at least binary system n-digit numerical value information, and identifying the type of the object based on the discrete identification information expressed as the at least binary system n-digit numerical value information, and the biological substance bound to the object for which the discrimination of the type is performed is detected or quantitatively measured using, as an indicator originating from the biological substance, atoms, molecules or substances which are contained in the biological substance but are not contained in the object.

Atoms, molecules or substances which are contained in the biological substance possessed by the biological substance bound object but are not contained in the object may appropriately be selected according to the type of biological substance. For example, if the biological substance is a nucleic acid, they may be selected from carbon atoms, phosphor atoms, nitrogen atoms, nucleic acid bases, sugars and phosphoric acids. If the biological substance is a peptide nucleic acid, they may be selected from, for example, carbon atoms, nitrogen atoms and nucleic acid bases. Further, if the biological substance is a peptide, a protein, an enzyme or an antibody, they may be selected from, for example, carbon atoms, nitrogen atoms and sulfur atoms.

In addition, the present invention also provides a method for detecting, identifying or quantitatively measuring so called a target substance which is uniquely bound to a probe of a prove bound object given a label.

The method for detecting, identifying or quantitatively measuring a target substance according to the present invention is a method comprising at least the steps of:

(1) reacting the probe bound object set force in any of claims 1 to 11 with a target substance to obtain a hybrid body; and (2) forming the composition condition of contained atoms corresponding to at least binary system n-digit numerical value information using the number (n) of types of atoms selected beforehand and the presence/absence of the selected individual atoms contained or the level of the contents thereof, whereupon using a label given to a bound object in which the hybrid body is formed using a label element having a composition satisfying the composition condition of the contained atoms, and identifying the presence/absence of the individual atoms contained or the level of the contents thereof for the plurality of types of atoms selected beforehand in the composition possessed by the label element using detection means for detecting the presence/absence of the atom contained or the level of the content thereof for the plurality of individual atoms selected beforehand, discriminating the composition condition of the contained atoms satisfied in the composition of the label element and extracting corresponding at least binary system n-digit numerical value information, detecting, identifying and quantitatively measuring a probe bound to a bound object in which the hybrid body is formed, by the method described previously, as necessary, and simultaneously or subsequently detecting, identifying and quantitatively measuring a target substance forming the hybrid body using as an indicator atoms, molecules or substances which are contained in the target substance but are not contained in the probe bound object and the probe.

In the methods described above, if an object is situated on a flat surface, it is preferable that a step of two-dimensionally imaging the flat surface on which the object is situated is further provided for identifying at least the position of the object on the flat surface when identifying the presence/absence of the individual atoms contained or the level of the contents thereof for the plurality of types of atoms selected beforehand in the composition possessed by the label element and when detecting the target substance.

For example, as detection means for detecting the presence/absence of the atom or the level of the content thereof for each of the plurality, of types of atoms selected beforehand, mass spectrometry may be used, and particularly, mass spectrometry which can suitably be used is time-of-flight secondary ion mass spectrometry (TOF-SIMS). As detection means for detecting the presence/absence of the atom contained or the level of the content thereof for each of the plurality of types of atoms selected beforehand, X-ray photoelectron spectroscopy (XPS) or Auger electron spectroscopy (AES) can also be used.

As atoms which are contained in the target substance but are not contained in the biological substance bound object and the biological substance, halogen atoms and metal atoms can suitably be used. In some cases, the aforementioned halogen atoms and metal atoms may be given to a target substance as so called a label. When metal atoms are introduced as a label, use of an organic metal complex or a substance containing an organic metal complex facilitates the introduction in some cases.

As an example of the aforementioned organic metal complex, use of the following compound (Sigma Aldrich) allows ruthenium to be introduced into a target substance using an amino group of the target substance. Bis(2,2'-bipyridine)-4'-methyl-4-carboxybipyridine-ruthenium N-succinimidyl ester-bis(hexafluorophosphate If the target substance is a nucleic acid, an aspect in which the halogen atom or metal atom is bound to the primer or dATP, dGTP, dCTP, dTTP (or dUTP), ATP, GTP, CTP or UTP for use in a primer elongation reaction when enzymically synthesizing the nucleic acid by the primer elongation reaction on the basis of a matrix nucleic acid can be a preferred aspect of the present invention. If the biological substance is a peptide nucleic acid and the target substance is a nucleic acid, atoms and the like specific to the target substance may include phosphor atoms and phosphoric acids. The substance to be bound with probes, probes themselves or target substances which have been described above can be mutually separately detected by the label element of the substance according to the present invention and the detection means for use in the present invention.

The method for detecting a label element in the present invention will now be described further in detail.

The aspect described above in which mass spectrometry is used as detection means for detecting the presence/absence of the atom contained or the level of the content thereof for each of a plurality of types of atoms selected beforehand is possible. At this time, the mass spectrometry is more preferably time-of-flight secondary ion mass spectrometry (TOF-SIMS). Alternatively, the aspect in which X-ray photoelectron spectroscopy (XPS) or Auger electron spectroscopy (AES) is used as, detection means, for detecting the presence/absence of the atom contained or the level of the content thereof for each of the plurality of types of atoms selected beforehand is also possible. The same method may be used for detection, identification and quantitatively measurement of an biological substance bound to the biological substance bound object.

When TOF-SIMS, XPS or AES is used, these analysis methods are also applicable to analysis of a measurement object extending two-dimensionally, and for example, if the object is situated on a flat surface, an aspect in which a step of two-dimensionally imaging the flat surface on which the object is situated is further provided when identifying the presence/absence of the individual atoms contained or the level of the contents thereof for the plurality of types of atoms selected beforehand in the composition possessed by the label element, and when detecting, identifying or quantitatively measuring the biological substance or the target substance bound to the biological substance. This holds true for a case where a plurality of objects are placed on a flat surface is also possible.

For explaining the performance of a detecting apparatus required in the present invention taking TOF-SIMS as an example for the detecting apparatus, the label element for use in the present invention is constituted by atoms, the mass thereof is 100 at most, and the sufficient mass resolution is basically 1 ms (mass unit). For detection, identification and quantitatively measurement of the biological substance and the target substance, the upper limit of mass is several hundreds at most, and the sufficient resolution is 1 ms. For TOF-SIMS, measurement of a high-mass substance and high-resolution measurement require a longer flight tube, a high primary ion speed, a high voltage for drawing secondary ions, and so on, and accordingly, the apparatus has an increased size, is expensive and has a high running cost.

In contrast to this, an apparatus required in the present invention can have a reduced size and be inexpensive.

In the method for labeling an object according to the present invention, the label element given to an object as a target uses information included in the composition, which is shown by the presence/absence of atoms contained or the level of the contents thereof for a plurality of types (n types) of atoms selected beforehand. Specifically, when one type of atom is selected from, for example, mutually different n types of elements as a plurality of types (n types) of atoms selected beforehand, whereupon the presence/absence of the atom contained (two levels) is changed for each type of atom, the total number $N_{TOTAL}$ of types of compositions including at least one of a plurality of types (n types) of atoms selected beforehand is $N_{TOTAL} = \Sigma nCm = 2^n - 1$ ($1 \leq m \leq n$, m and n are positive integers). Alternatively, when for each atom, the content thereof is changed in two stages (two levels) of, for example, "very small amount and small amount", at least a plurality of types (n types) of atoms selected beforehand are included, and the total number $N_{TOTAL}$ Of types of compositions having a difference, in their contents is $N_{TOTAL} = 2^n$.

When for a plurality of types (n types) of atoms selected beforehand, the contents thereof are changed in three stages (three levels) of, for example, "no atom contained, very small amount and small amount", the total number $N_{TOTAL}$ of types of compositions including at least one of a plurality of types (n types) of atoms selected beforehand is $N_{TOTAL} = 3^n - 1$.

Further, when for one specific type of atom among a plurality of types (n types) of atoms selected beforehand, the content thereof is changed in three stages (three levels) of, for example, "no atom contained, very small amount and small amount", and for the remaining (n−1) types of atoms, presence/absence of atoms contained (two levels) is changed, the total number $N_{TOTAL}$ of types of compositions including at least one of a plurality of types (n types) of atoms selected beforehand is $N_{TOTAL} = 3 \times (2^n - 1) - 1$. Formally, the aspect described above corresponds to an aspect in which for all of a plurality of types (n types) of atoms selected beforehand, indicators of three stages (three levels) of, for example, "no atom contained, very small amount and small amount" are set, whereupon for one specific type of atom, the content thereof is changed while being associated with, indicators of three stages (three levels), but for the remaining (n−1) types of atoms, only two types of indicators of "no atom contained and small amount" are selected among indicators of three stages (three levels). Specifically, it corresponds to an aspect in which among the total number of types of settable compositions $N_{TOTAL} = 3^n - 1$, $\{3 \times (2^n - 1) - 1\}$ types, as its subset are selected and used. Thus, for a plurality of types (n types) of atoms selected beforehand, the content thereof is divided into sections of three stages (three levels) or more to multiply options, whereby the range of the total number $N_{TOTAL}$ of types of compositions can be expanded, for example, until $\{M^n - 1\}$ types are achieved when the content is sectioned into M stages (M levels).

As described above, a plurality of types of atoms are selected beforehand as a label element given to an object as a target, and information included in the composition, which is shown by the presence/absence atoms contained or the level of the contents thereof for this number of types (n types) of atoms is used, whereby the number of types of labels for achieving $N_{TOTAL} = 2^n - 1$ can be given only by changing the content for at least a plurality of types (n types) of atoms selected beforehand. For example, the number of types of labels for achieving $N_{TOTAL} = 2^n - 1$ corresponds to at least binary system n-digit numerical value when a plurality of types (n types) of atoms selected beforehand are associated with each digit.

Since the label element given an object as a target uses information included in the composition, the number (n) of types of atoms selected beforehand is preferably selected as appropriate according to the total number of types of targeted labels. For example, if the number (n) of types of atoms selected beforehand is 5 or more, the total number $N_{TOTAL}$ of types of compositions is at least $N_{TOTAL} = \{2^5 - 1\}$ or more, specifically it can be applied to 31 types or more as the total number of types of targeted labels, using as an indicator the presence/absence of atoms contained or the level of the contents thereof. For example, for identification of various kinds of bacteria, gene information specific to individual bacteria, for example rRNA base sequences can be used. For selection of a code region on a genome gene, it is necessary to carry out a DNA hybridization assay using DNA probes having a variety of base sequences. More specifically, there are not a few cases where the number of types of DNA probes used exceeds 31 in identification of infectious disease causing bacteria using the DNA hybridization assay. In this case, 255 or more types of labels an be given by applying the labeling method according to the present invention to a particulate base on which each DNA probe is fixed so that the number (n) of types of atoms selected beforehand is 8 or more. For a single base polytype found in the human genome gene, types far exceeding 255 types have been reported, and it is desirable that for DNA probes for use in detection of individual single base polytypes, discrimination should be performed by labels given to particulate bases which are used for fixation of the probes. For example, if the number (n) of types of atoms selected beforehand is 12 or more, 4095 or more types of labels can be given, and labels corresponding to a considerable part of the single base polytype (SNP) found in the human genome gene can be provided. Further, if the number (n) of types of atoms selected beforehand is 16 or more, 65535 or more types of labels can be given, and for example, a peculiar label can be provided to each of an enormously large number of DNA probes corresponding to all genes existing, in the human genome. Thus, the labeling method according to the present invention can properly increase and decrease the number (n) of types of atoms selected beforehand, which is used for expression of label information, in accordance with the total number of types of targeted labels, and has extensibility making it possible, to accommodate an extremely wide range of applications, such that various probe molecules that are used in various kinds of assays are mutually discriminated by label elements given to particulate bases for, use in fixation of the probe molecules.

For example, in the method disclosed in Japanese Patent Application Laid-Open No. H01-095800, labeled particles using a particular single type of metal element are used for micro-beads for fixation of each DNA probe, whereby the single type of metal element is analyzed using fluorescent X-rays to identify the type of each DNA probe. This labeling, method has a configuration in which as a label element, one type of metal element such as Cr, Fe, Zn, Ba or Ti is used as label information of one character. Thus, this method is different in the technical idea from a technique in which a plurality of types (n types) of atoms selected beforehand are used to express label information corresponding to, for example, binary system n-digit numerical value information with the level of the contents of the atoms as an indicator as in the label method according to the present invention. In the method disclosed in Japanese Patent Application Laid-Open No. H07-083927, a plurality of types of inorganic fluorescent substances are used to prepare an ultrafine particle material for fixing probe molecules, and a fluorescence characteristic of each of such inorganic fluorescent substances is observed to identify the type of each probe molecule. This labeling method has a configuration in which as a label element, a fluorescence characteristic of each of a plurality of types of inorganic fluorescent substances is used as label information of one character. Thus, this method is different in the technical idea from a technique in which a plurality of types (n types) of atoms selected beforehand are used to express label information corresponding to, for example, binary system n-digit numerical value, information with the level of the contents of the atoms as an indicator as in the label method according to the present invention.

For explaining the feature of the technical idea more in detail, in the labeling method according to the present invention, apparently, 5 types of atoms are selected beforehand and used for labeling, but in essence, for example, 16 types are selected as a plurality of types (n types) of atoms selected beforehand, whereupon the atoms are assigned to corresponding digits to be matched with, for example, binary system 16-digit numerical value information, whereupon among them, only 5 types of atoms are arbitrarily selected, and $\{2^5-1\}$ types are used as a subset using as an indicator the presence/absence of the atoms contained. Specifically, the method is extensible to a sufficiently wide range of applications beforehand, but according to the range of applications, a subset as a part of the range is used.

In the labeling method according to the present invention, the shape and size of the object itself can arbitrarily be selected as long as information of the content for specific atoms can be used as a label element. For example, in the case of fine particles for use in fixation of various kinds of probe molecules, fine particles of indeterminate forms including acicular forms, stick forms, irregularities and the like, and fine particles of determinate forms including spherical forms, quadrate forms and the like are suitable. In addition, when bases for use in fixation of various kinds of probe molecules are fibrous and sheeted objects, the method for labeling an object according to the present invention can suitably be applied. In addition, the material of fine particles for use in fixation of various kinds of probe molecules can be a magnetic material, and selection of a form of such magnetic fine particles makes it possible to apply an operation of separation from a liquid phase using a magnetic force in a state of fixing various kinds of probe molecules.

For example, when the method for labeling an object according to the present invention is applied to fine particles that can be used for fixation of various kinds of probe molecules, a configuration in which the composition of a material constituting the fine particles themselves is variously changed, so that for a plurality of types (n types) of atoms selected beforehand, the presence/absence or the level of the content is varied to give labels may be employed. A dry method in which raw materials adjusted to have a desired composition ratio are mixed, baked and ground, a coprecipitation method in which a coprecipitate containing a plurality of types of atoms is obtained from a solution adjusted to have a desired composition ratio, and a spray decomposition method in which a raw material is dissolved, thermally decomposed by spray and ground can be used. For example, using the method for producing oxide superconductive material fine particles, which is disclosed in Japanese Patent. Application. Laid-Open No. S64-051322, oxide fine particles containing in the form of oxides a plurality of types (n types) of metal atoms selected beforehand can be formed. Using the method for producing ferrite particles using a coprecipitation method, which is disclosed in Japanese Patent Application Laid-Open No. 2002-128523, ferrite particles containing a plurality of types (n types) of metal atoms selected beforehand can be formed.

Further, a configuration in which coated fine particles prepared by adding coated layers to nucleic fine particles formed of various kinds of materials are formed, and the composition of the material of the coated layers is variously changed, so that for a plurality of types (n types) of atoms selected beforehand, the presence/absence or the level of the content is varied to give labels may be employed. For example, using particles of glass, plastic, silicon, metals and, the like as nucleic fine particles, coated layers having a desired composition can be formed by the means described below. For example, as the dry method, a PVD (physical vapor deposition) method such as vacuum deposition, ion plating or sputtering, a CVD method (chemical vapor deposition) method, or coated layer formation applying the air dispersion method disclosed in Japanese Patent Application Laid-Open No. H07-053271 may be used. Further, instead of the coated layer, a desired element may be introduced into the surface of nucleic fine particles using an ion implantation method, and the composition of the surface areas may be changed to form surface layers.

In the method for labeling an object according to the present invention, a plurality of types, (n types) of atoms selected beforehand, which are included in composition components constituting label elements are not specifically limited as long as their types can be identified with high accuracy and their contents can be measured with good repeatability. However, there is a certain limitation on elements that can be used in terms of retainment of performances required for an object itself as a target, for example magnetic material properties. In addition, there are elements that cannot be used in principle depending on the production method. Thus, it is preferable that a plurality of types (n types) of atoms used are appropriately selected in consideration of performances required for an object itself as a target and the production method. At this time, elements satisfying the above conditions are preferably selected from, for example, typical metal elements and transition metal elements.

As one example, examples of a combination of a plurality of types of atoms used may include, for example, a combination of Co, Ni, Mn, Zn, Cu, Mg, Al and Ti for 8 types, a combination of Co, Ni, Mn, Zn, Cu, Mg, Al, Ti, Ga, Ge, Ag and Pd for 12 types, and a combination of Co, Ni, Mn, Zn, Cu, Mg, Al, Ti, Ga, Ge, Ag, Pd, V, Cr, Ru and Rh for 16 types.

For the method for analyzing and detecting an object given a label according to the present invention, any analysis method can be used as long as it is a method for labeling an object according to the present invention, specifically means capable of identifying the presence/absence of atoms contained or the level of the contents thereof for a plurality of types of atoms selected beforehand, which are used as label elements. For example, mass spectrometry such as time-of-flight secondary ion mass spectrometry (TOF-SIMS), X-ray photoelectron spectroscopy (XPS) and Auger electron spectroscopy (AES) may suitably be used. Further, these methods are capable of two-dimensional imaging and can also be used as a detection method when a plurality of different particles exist in a two-dimensional form.

(Embodiment of Nucleic Acid Primer Bound Object)

A nucleic acid primer bound object can be provided by using a nucleic acid primer as an biological substance as described above.

For the nucleic acid primer, single strand nucleic acid molecules having desired base sequences are used, and the nucleic acid primer may be bound covalently to the surface of the object directly or indirectly via a linker at the 5' terminal side of the primer.

Further, the present invention provides a method for identifying, detecting or quantitatively measuring a nucleic acid primer bound to a nucleic acid primer bound object given a label according to the present invention.

Specifically, the method for identifying, detecting or quantitatively measuring a nucleic acid primer bound to an object according to the present invention is a method for identifying, detecting or quantitatively measuring a nucleic acid primer bound to a nucleic acid primer bound object according to the present invention, which has the aforementioned configuration, wherein the type of the object, specifically the type of nucleic acid primer bound to the object is discriminated by using a label of the object given using the label element, and identifying the presence/absence of individual atoms contained or the level of the contents thereof for the plurality of types of atoms selected beforehand in the composition possessed by the label element using detection means for detecting the presence/absence of the atom contained or the level of the content thereof for the plurality of types of atoms selected beforehand, discriminating the composition condition of the contained atoms which is satisfied in the composition of the label element, and extracting corresponding at least binary system n-digit numerical value information, and identifying the type of the object based on the discrete identification information expressed as the at least binary system n-digit numerical value information, and the nucleic acid primer bound to the object for which the discrimination of the type is performed is detected or quantitatively measured using, as an indicator originating from the nucleic acid primer, atoms, molecules or substances which are contained in the nucleic acid primer but are not contained in the object.

In addition, the present invention provides a method for using a nucleic acid primer bound object according to the present invention to detect a single nucleotide polytype (SNP) of a target nucleic acid applying a nucleotide elongation reaction.

The method for detecting a single nucleotide polytype (SNP) of a target nucleic acid according to the first embodiment of the present invention is a method for detecting a single nucleotide polytype of a target nucleic acid using a nucleic acid primer bound material, wherein the step of detecting a single nucleotide polytype existing in the target nucleic acid comprises at least the following steps of:

(1) preparing at least one type of nucleic acid primer bound object which is the nucleic acid primer bound object according to the present invention having the aforementioned configuration, wherein as a nucleic acid primer bound to the surface of an object given the label, at least one type of nucleic acid primer having a base sequence complementary to a region consisting of a nucleotide showing a single nucleotide polytype as a detection target existing in a base sequence of the target nucleic acid and a partial base sequence on the 3' terminal side thereof and containing on the 3' terminal a nucleotide complementary to the nucleotide showing the single nucleotide polytype, and constituted by a nucleic acid strand showing a predetermined base length is selected;

(2) placing the target nucleic acid having the single nucleotide polytype as a detection target and at least one type of nucleic acid primer bound object prepared in the step (1) under conditions allowing formation of a hybrid body between the nucleic acid primer and the target nucleic acid to form the hybrid body, and then subjecting the formed hybrid body to nucleic acid strand elongation to the 3' terminal side of the nucleic acid primer with the target nucleic acid as a matrix under conditions allowing an enzymic nucleic acid strand elongation reaction in an enzyme reaction solution containing a polymerase enzyme involved in the enzymic nucleic acid strand elongation reaction, at least one type of nucleoside triphosphate for use as a base in the enzymic nucleic acid strand elongation reaction and a nucleoside triphosphate having a label substance bound thereto, and capturing the nucleoside having the label substance bound thereto in the nucleic acid strand elongated to: the 3' terminal side of the nucleic acid primer; and (3) detecting elongation of the nucleic acid strand to the 3' terminal side of the nucleic acid primer by detecting the nucleoside having the label substance bound thereto, captured in the elongated nucleic acid strand, using the label substance as an indicator, for the nucleic acid primer bound object in which the nucleic acid strand is elongated to the 3' terminal side of the nucleic acid primer, and forming the composition condition of contained atoms corresponding to at least binary system n-digit numerical value information using the number (n) of types of atoms selected beforehand, and the presence/absence of the selected individual atoms, contained, or the level of the contents thereof, for the nucleic acid primer bound object in which elongation of the nucleic acid strand to the 3' terminal side of the nucleic acid primer is detected, whereupon using labels given to the object using label elements having compositions satisfying the composition condition of the contained atoms, identifying the presence/absence of individual atoms contained or the level of the contents thereof for the plurality of types of atoms selected beforehand in the composition possessed by the label element using detection means for detecting the presence/absence of the atom contained or the level of the content thereof for the plurality of types of atoms selected beforehand, discriminating the composition condition of the contained atoms which is satisfied in the composition of the label element, and extracting corresponding at least binary system n-digit numerical value information, and identifying the type of the nucleic acid primer bound object based on the discrete identification information expressed as the at least binary system n-digit numerical value information, and further, identifying a base sequence possessed by the nucleic acid primer bound to the nucleic acid primer bound object.

In the step (2), when the hybrid body of the target nucleic acid and the nucleic acid primer is formed, the 3' terminal of the nucleic acid primer is in a position opposite to a nucleotide site showing the single nucleotide polytype of the detection target existing in the base sequence of the target nucleic acid. If the base at the 3' terminal of the nucleic acid primer and the base of the single nucleotide polytype site of the detection target are actually complementary, a double strand structure (base pair) is formed at the 3' terminal site of the nucleic acid primer, and the elongation reaction of the nucleic acid strand proceeds with the target nucleic acid as a matrix. If the base at the 3' terminal of the nucleic acid primer and the base of the single nucleotide polytype site of the detection target are not complementary, the double strand structure (base pair) is not formed at the 3' terminal site of the nucleic acid primer, and the elongation reaction of the nucleic acid strand does not proceed with the target nucleic acid as a matrix. Specifically, if the elongation of the nucleic acid strand of at least one nucleotide occurs, it demonstrates that the base of the 3' terminal of the nucleic acid primer and the base of the single nucleotide polytype of the detection target are actually complementary.

In this first embodiment, in addition to at least one type of nucleoside triphosphate for uses as a base for a polymerase enzyme, a nucleoside triphosphate having a label substance bound thereto is added in a reaction solution in the elongation reaction of the nucleic acid strand, and a nucleoside having a label substance bound thereto is captured with a certain frequency in the nucleic acid strand that is elongated. Actually, for capturing a nucleoside having a label substance bound thereto in the nucleic acid strand that is elongated, the nucleoside having a label substance bound thereto should be capable of forming a base pair with the complementary nucleoside existing in the target nucleic acid as a matrix. In other words, in the nucleoside having a label substance bound thereto, the bound label substance should not hinder the formation of the base pair, and should not hinder the coupling to the 3' terminal of the nucleic acid strand. The nucleoside triphosphate constituting the nucleoside triphosphate having the label substance coupled thereto is selected from the group consisting of dATP, dGTP, dCTP, dTTP (or dUTP), ddATP, ddGTP, ddCTP, ddTTP (or ddUTP), ATP, GTP, CTP and UTP according to the type of polymerase enzyme involved in the enzymatic nucleic acid strand elongation reaction. When the label substance is bound on the base part in the selected nucleoside triphosphate, it is necessary to select the binding position in a site not hindering the formation of the base pair or to select the label substance bound and the binding position so as to retain a base pair forming capability equivalent to that of an original base.

The base sequence of the nucleic acid strand elongated is complementary to the base sequence positioned on the 5' terminal side from the nucleotide site showing the single nucleotide polytype of the detection target existing in the base sequence of the target nucleic acid. Since the base sequence of the target nucleic acid is already known and hence, the base sequence of the nucleic acid strand elongated can be identified, the frequency with which the nucleoside having a label substance bound thereto is captured in the nucleic acid strand elongated can be predicted. It is desirable to select the type of base forming the nucleoside triphosphate having a label substance bound thereto so that the frequency with which the nucleoside having a label substance bound thereto exceeds a desired frequency in consideration of the base sequence of the nucleic acid strand elongated. For example, it is desirable to select a type of base forming the nucleoside triphosphate having a label substance bound thereto from bases contained in a 5 base long base sequence complementary to a 5 base long partial base sequence on the 5' terminal side of the nucleotide site showing the single nucleotide polytype of the detection target using the nucleotide site as a basis. Particularly, a base complementary to a base adjacent to the 5' terminal side of the nucleotide site showing the single nucleotide polytype of the detection target using the nucleotide site as a basis is more preferably selected as a type of base forming the nucleoside triphosphate having a label substance coupled thereto.

In the step (3), the elongation of the nucleic acid strand to the 3' terminal side of the nucleic acid primer is detected based on the presence/absence of a nucleoside bound to the label substance captured in the nucleic acid strand elongated, or using the label substance as an indicator. The type of nucleic acid primer in which the elongation of the nucleic acid strand occurs is identified by identifying a label given to an object to which the nucleic acid primer is bound. Specifically, in the labeling method for use in the present invention, multiple types of labels can be given, and when treating multiple types of nucleic acid primers, the type of nucleic acid primer bound to an object given a specific label can be matched on a one-to-one basis at the time of preparing the nucleic acid primers. In other words, it is not necessary to analyze the nucleic acid primer itself for identifying the base sequence of the nucleic acid primer itself bound to the surface of the object.

If the nucleic acid primer bound object in which the nucleic acid strand is elongated to the 3' terminal side of the nucleic acid primer is situated on a flat surface, it is preferable that a step of two-dimensionally imaging the flat surface on which the object is situated is further provided for identifying at least the position of the object on the flat surface, when detecting the presence/absence of individual atoms contained or the level of the contents thereof, and the labeling substance for the plurality of types of atoms selected beforehand in the composition possessed by the label element. In particular, when a plurality of objects are situated on different regions on the same flat surface on the surface where the nucleic acid primer bound object in which the nucleic acid strand is elongated to the 3' terminal side of the nucleic acid primer is situated, it is preferable that a step of two-dimensionally imaging, the surface on which the objects are situated is further provided for identifying at least the positions of the objects on the flat surface.

As detection means for detecting the presence/absence of atoms contained or the level of the contents thereof for the plurality of types of individual atoms selected beforehand and means for detecting the label substance, mass spectrometry is preferably used. Particularly, mass spectrometry that can suitably be used is time-of-flight secondary ion mass spectrometry (TOF-SIMS). Alternatively, As detection means for detecting the presence/absence of atoms contained or the level of the contents thereof for the plurality of types of individual atoms selected beforehand and means for detecting the label substance, X-ray photoelectron spectroscopy (XPS) or Auger electron spectroscopy (AES) can also be used.

The method for detecting the single nucleotide polytype (SNP) of the target nucleic acid according to the first embodiment of the present invention can have a configuration in which detection is carried out using a plurality of types of nucleic acid primer bound objects prepared by binding to different types of objects a plurality of types of nucleic acid primers different only in the base corresponding to the single nucleotide polytype (SNP) site as nucleic acid primers bound to the surface of the object given a label. At this time, the elongation of the nucleic acid strand occurs only in nucleic acid primer bound objects having at the 3' terminal a base complementary to a base actually existing at the single nucleotide polytype (SNP) site in the target nucleic acid among a plurality of types of nucleic acid primer bound objects. Thus, an aspect in which for a plurality of objects to which a plurality of different nucleic acid primers are bound, the type of object, specifically the type of nucleic acid primer bound to the object is discriminated only for nucleic acid primer bound objects in which the elongation reaction from the nucleic acid primer occurs when the objects are placed under conditions for the nucleic acid elongation reaction from the nucleic acid primer is also possible.

The method for detecting a single nucleotide polytype (SNP) of a target nucleic acid according to the second embodiment of the present invention is a method for detecting a single nucleotide polytype of a target nucleic acid using a nucleic acid primer bound material, wherein the step of detecting a single nucleotide polytype existing in the target nucleic acid comprises at least the following steps of:

(1) preparing at least one type of nucleic acid primer bound object which is the nucleic acid primer bound object according to the present invention having the aforementioned configuration, wherein as a nucleic acid primer bound to the surface of an object given the label, at least one type of nucleic acid primer having a base sequence complementary to a region consisting of a nucleotide showing a single nucleotide polytype as a detection target existing in a base sequence of the target nucleic acid and a partial base sequence on the 3' terminal side thereof, and constituted by a nucleic acid strand showing a predetermined base length is selected;

(2) placing the target nucleic acid having the single nucleotide polytype as a detection target and at least one type of nucleic acid primer bound object prepared in the step (1) under conditions allowing formation of a hybrid body between the nucleic acid primer and the target nucleic acid to form the hybrid body, and then subjecting the formed hybrid body to nucleic acid strand elongation to the 3' terminal side of the nucleic acid primer with the target nucleic acid as a matrix under conditions allowing an enzymic nucleic acid strand elongation reaction in an enzyme reaction solution containing a polymerase enzyme involved in the enzymic nucleic acid strand elongation reaction and 4 types of dideoxynucleoside triphosphates: at least one of {ddATP, ddGTP, ddCTP and ddTTP} and {ddATP, ddGTP, ddCTP and ddUTP}, to which different label substances capable of being used as a base for the polymerase enzyme are bound, and capturing on the 3' terminal side of the nucleic acid primer the dideoxynucleoside having the label substance; and (3) identifying the type of base of the dideoxynucleoside elongated to the 3' terminal side of the nucleic acid primer by detecting the dideoxynucleoside captured on the 3' terminal side and having the label substance bound thereto using the label substance as an indicator for the nucleic acid primer bound object in which the dideoxynucleoside having the label substance bound thereto is captured on the 3' terminal side of the nucleic acid primer, and forming the composition condition of contained atoms corresponding to at least binary system n-digit numerical value information using the number (n) of types of atoms selected beforehand, and the presence/absence of the selected individual atoms contained, or the level of the contents thereof, for the nucleic acid primer bound object in which the capture of the dideoxynucleoside on the 3' terminal side of the nucleic acid primer is detected, whereupon using labels given to the object using label elements having compositions satisfying the composition condition of the contained atoms, identifying the presence/absence of individual atoms contained or the level, of the contents thereof for the plurality of types of atoms selected beforehand in the composition possessed by the label element using detection means for detecting the presence/absence of the atom contained or the level of the content thereof for the plurality of types of atoms selected beforehand, discriminating the composition condition of the contained atoms which is satisfied in the composition of the label element, and extracting corresponding at least binary system n-digit numerical value information, and identifying the type of the nucleic acid primer bound object based on the discrete identification information expressed as the at least binary system n-digit numerical value information, and further, identifying a base sequence possessed by the nucleic acid primer bound to the nucleic acid primer bound object.

In the step (2), when the hybrid body of the target nucleic acid and the nucleic acid primer is formed, the 3' terminal of the nucleic acid primer is in a position opposite to a base adjacent to the 3' terminal side of a nucleotide site showing a single nucleotide polytype of the detection target existing in the base sequence of, the target nucleic acid using the nucleotide site as a basis. Since the base at the 3' terminal of the nucleic acid primer and the base adjacent to the 3' terminal side of the single nucleotide polytype site of the detection target are actually complementary, a double strand structure (base pair) is formed at the 3' terminal site of the nucleic acid primer, and an elongation reaction of the nucleic acid strand starts with a target nucleic acid as a matrix. Specifically, in the target nucleic acid as a matrix, the nucleotide of the base complementary to the base actually existing in the single nucleotide polytype site of the detection target is first coupled to the 3' terminal of the nucleic acid primer.

In the second embodiment, in the elongation reaction of the nucleic acid strand, 4 types of dideoxynucleoside triphosphates: at least one of {ddATP, ddGTP, ddCTP and ddTTP} and {ddATP, ddGTP, ddCTP and ddUTP}, to which different label substances capable of being used as a base for the polymerase enzyme are bound, are added in the enzyme reaction solution. Specifically, a dideoxynucleoside which has a base complementary to a base actually existing at the single nucleotide polytype site of the detection target and to which a label substance is bound is coupled to the 3' terminal of the nucleic acid primer. In this dideoxynucleoside, hydroxy groups at the 3' position and 2' position of the sugar part do not exist, and therefore elongation of subsequent nucleic acid strands is impossible. Specifically, if the type of base of the dideoxynucleoside coupled to the 3' terminal of the nucleic acid primer and having a label substance bound thereto is known, the base actually existing at the single nucleotide polytype site of the detection target can be determined to be the complementary base. Different label substances are bound to 4 types of dideoxynucleoside triphosphates, and the type of base of the dideoxynucleoside captured is identified with a label substance as an indicator.

In fact, for capturing the dideoxynucleoside having a label substance bound thereto at the 3' terminal of the nucleic acid primer, the dideoxynucleoside having a label substance bound thereto should be capable of forming a base pair with a nucleoside actually existing at the single nucleotide polytype site existing in the target nucleic acid as a matrix. In other words, in the nucleoside having a label substance bound thereto, the bound label substance should not hinder the formation of the base pair, and should not hinder the coupling of the nucleoside itself having a label substance bound thereto to the 3' terminal of the nucleic acid strand.

In the step (3), detection of the presence/absence of the dideoxynucleoside coupled to the 3' terminal side of the nucleic acid primer and having the label substance bound thereto, and the type of base thereof is performed by detecting the type of label substance as an indicator. Identification of the type of the nucleic acid primer of which the label substance is detected, specifically the base sequence of the probe part is performed by identifying the label given to an object to which the nucleic acid primer is bound.

For example, when the nucleic acid primer bound to the surface of the object is synthesized directly on the surface of the object by a solid phase sequential synthesis, single strand nucleic acid molecules having targeted base sequences and occupied by nucleic acid primers of a predetermined base length for the most part, but having the base length reduced by slight deletion of bases in targeted base sequences are mingled. If deletion of bases occurs at some midpoints of the base sequence, the base length fit for the base sequence of the target nucleic acid is short and its 3' terminal cannot form a base pair, and therefore the probability of occurrence of elongation of the nucleic acid strand to the 3' terminal of the single strand nucleic acid molecule having the base length reduced with the target nucleic acid as a matrix. However, if the deleted base happens to be at the 3' terminal of the targeted base sequence, the single strand nucleic acid molecule having the base length reduced has a completely fit base sequence, and elongation of the nucleic acid strand occurs at the 3' terminal. Conversely, if the 3' terminal of the base sequence possessed by the nucleic acid primer bound to the surface of the object is not complementary to the base of the target nucleic acid as a matrix and cannot form a base pair, the single strand nucleic acid molecule in which the base of the 3' terminal happens to be deleted and the base length is reduced has a completely fit base sequence, and elongation of the nucleic acid strand occurs at the 3' terminal.

The dideoxynucleoside having a label substance bound thereto, which is coupled to the 3' terminal of such, a mingled single strand nucleic acid molecule in which only the base at the 3' terminal is deleted and the base length is reduced is not complementary to a base of the single nucleotide polytype site of the detection target but complementary to a base adjacent to the 3' terminal side. The collateral product and the desired elongation product have a quantitative difference, and therefore they can easily be distinguished referring to the relative detection intensity of a detected label substance. In addition, by identifying a label given to an object of which the label substance is detected and to which the nucleic acid primer is bound, the type of the nucleic acid primer, specifically the base sequence of the probe part is identified, thus making it possible to verify whether the product is a collateral product or a desired elongation product.

If the nucleic acid primer bound object in which the dideoxynucleoside is captured on the 3' terminal side of the nucleic acid primer is situated on a flat surface, it is preferable that a step of two-dimensionally imaging the flat surface on which the object is situated is further provided for identifying at least the position of the object on the flat surface when detecting the presence/absence of individual atoms contained or the level of the contents thereof for the plurality of types of atoms selected beforehand in the composition possessed by the label element, and the label substance. In particular, when a plurality of objects are situated on different regions on the same flat surface on the surface on which the nucleic acid primer bound object in which the dideoxynucleoside is captured on the 3' terminal side of the nucleic acid primer is situated, it is more preferable that a step of two-dimensionally imaging the flat surface on which the object is situated is further provided for identifying at least the positions of the objects on the flat surface.

In the method for detecting a single nucleotide polytype (SNP) of the target nucleic acid according to the second embodiment of the present invention, a base complementary to a base actually existing at the single nucleotide polytype (SNP) site is elongated to the 3' terminal in the target nucleic acid for the nucleic acid primer bound substance. Thus, among 4 types of dideoxynucleoside triphosphates: at least one of {ddATP, ddGTP, ddCTP and ddTTP} and {ddATP, ddGTP, ddCTP and ddUTP} which are contained in an enzyme reaction solution and to which different label substances are bound, a dideoxynucleoside having a base complementary to a base actually existing at the single nucleotide polytype (SNP) site is captured when an elongation reaction is carried out. For example, an aspect in which for a plurality of objects to which a plurality of different nucleic acid primers are bound, the type of object, specifically the type of nucleic acid primer bound to the object is discriminated only for nucleic acid primer bound objects in which the elongation reaction from the nucleic acid primer occurs when the objects are placed under conditions for the nucleic acid elongation reaction from the nucleic acid primer is also possible.

In the method for detecting a single nucleotide polytype (SNP) of the target nucleic acid according to the present invention, a nucleoside having a label substance bound thereto is captured in a nucleic acid stand elongated, and detection is carried out with the label substance as an indicator in both the first embodiment and second embodiment described above. As a label substance constituting the nucleoside having the label substance bound thereto, a fluorescent label which is used in normal nucleotide labeling can be used. At this time, the binding of the fluorescent label to a nucleoside should be carried out at a site where a complementary base on the target nucleic acid as a matrix and the nucleoside can form a base pair. Specifically, for introducing a fluorescent label into the nucleoside without hindering the formation of the base pair, for example, a method in which a fluorescent substance is bound to the 8 position of a purine base, the 5 position of a pyrimidine base, or the 2' position of a sugar via a linker may be used. Examples of nucleoside triphosphates which function as a base for a polymerase enzyme and retain an original base pair forming capability and to which a fluorescent compound is bound as a label substance include those having a florescent compound bound to the 2' position of a sugar via a linker.

If a fluorescence originating from a fluorescent compound bound to a nucleoside is used as a label substance when detecting the presence/absence of elongation of the nucleic acid strand or the type of captured nucleoside having a label substance bound thereto, a method in which a fluorescence specific to the fluorescent compound is detected by a fluorescence detecting apparatus such as a fluorescent microscope may be used. There are cases where in addition to a fluorescence originating from a desired elongation product, a fluorescence originating from a collateral product is measured at the same time when the nucleic acid primer bound object in which the nucleoside having a label substance bound thereto is captured is collected, and then the fluorescent label is detected. In this case, an analytical method in which the fluorescent intensity originating from the coexisting fluorescent compound is separated and a fluorescence originating from the desired elongation product is identified is preferably used.

In the first embodiment described above, there are cases where if a plurality of types of nucleoside triphosphates to which a fluorescent compound is bound as a label substance are added in an enzyme reaction solution, a plurality of types of nucleoside triphosphates in which a nucleoside to which a fluorescent compound is bound as a label substance is captured in the elongated nucleic acid strand are mixed. There are cases where when a plurality of types of fluorescent compounds are mixed, for example, a fluorescence emitted by one fluorescent compound is absorbed by another fluorescent compound, and resultantly, the apparent fluorescent intensity does not reflect a relative ratio of amounts of mixed fluorescent compounds. Thus, an analytical method of estimating an original fluorescent intensity originating from mixed fluorescent compounds is preferably used. Alternatively, in the first embodiment described above, analytical problems originating from mixed fluorescent compounds can be avoided by limiting nucleoside triphosphates which are added in the enzyme reaction solution and to which a fluorescent compound is, bound as a label substance to one type.

Normally, when a fluorescent compound is used as a label substance, it is desirable, to select an order in which the fluorescent label is detected by a fluorescence detecting apparatus such as a fluorescent microscope, and then a label given to an object to which a nucleic acid primer is bound is identified. If there is a sufficient amount of nucleic acid primer bound object capable of being used in evaluation and collected after the completion of the nucleic acid strand elongation reaction, a measurement operation for identifying a label given to the object and an operation for detecting a fluorescent label can be carried out separately using dispensed samples. If the captured fluorescent compound is not substantially influences when carrying out the measurement operation for identifying a label to the object, the operation for detecting a fluorescent label can be carried out after the measurement operation for identifying the label.

A method in which a label is given using halogen atoms and metal atoms as other label substances capable of being used in the nucleoside triphosphate to which a label substance is bound may be used. If halogen atoms are used as a label substance, use of fluorine, chlorine, bromine and iodine labels in correspondence to 4 types of bases {adenine, guanine, cytosine and thymine} or {adenine, guanine, cytosine and uracil} allows 4 types of bases to be individually labeled.

When metal atoms are introduced as a label into a nucleoside triphosphate functioning as a base for a polymerase enzyme, use of an organic metal complex containing the metal or a substance containing the organic metal complex may facilitate the introduction.

As an example of the organic metal complex described above, use of the following ruthenium-containing organic metal complex compound (Sigma Aldrich) allows ruthenium of a target substance to be introduced using an amino group existing in the nucleoside triphosphate.

Bis(2,2'-bipyridine)-4'-methyl-4-carboxybipyridine-ruthenium N-succinimidyl ester-bis(hexafluorophosphate The method for detecting a label element given to an object, which is used in the present invention, will now be described.

An aspect in which mass spectrometry is used as detection means for detecting the presence/absence of the atom contained or the level of the content thereof for each of a plurality of types of atoms selected beforehand, which has been described above, is also possible. At this time, the mass spectrometry is more preferably time-of-flight secondary ion mass spectrometry (TOF-SIMS). An aspect in which as detection means for detecting the presence/absence of the atom contained or the level of the content thereof for each of the plurality of types of atoms selected beforehand, X-ray photoelectron spectroscopy (XPS) or Auger electron spectroscopy (AES) is used is also possible.

When a nucleic acid primer bound to an object is detected or quantitatively measured, similar analysis means may be used as means for detecting an indicator originating from the nucleic acid primer. For example, when the aforementioned atoms are selected as an indicator originating from the nucleic acid primer, phosphorous atoms or carbon atoms and nitrogen atoms different in the binding state can be detected using X-ray photoelectron spectroscopy (XPS) or Auger electron spectroscopy (AES) to quantitatively measure the nucleic acid primer. Further, when the presence/absence of a nucleic acid strand elongated to the 3' terminal of the nucleic acid primer is detected, similar analysis means may be used as means for detecting a label substance existing in the nucleic acid strand elongated, depending on the type of the label substance. For example, when halogen atoms or metal atoms are used as a label substance existing in the nucleic acid strand elongated, halogen atoms or metal atoms can be detected using X-ray photoelectron spectroscopy (XPS) or Auger electron spectroscopy (AES) to quantitatively measure the label substance.

When TOF-SIMS, XPS or AES is used, these analysis methods are also applicable to a measurement object extending two-dimensionally, and for example, if the object is situated on a flat surface, an aspect in which a step of two-dimensionally imaging the flat surface on which the object is situated is further provided for the purpose of identifying the position of the object on the flat surface when identifying the presence/absence of the individual atoms contained or the level of the contents thereof for the plurality of types of atoms selected beforehand in the composition possessed by the label element. Particularly, if a plurality of objects are situated on different regions on the same flat surface, it is preferable that the regions on which the plurality of objects are situated are identified by two-dimensionally imaging the flat surface on which the objects are situated.

Further, in the method for identifying, detecting or quantitatively measuring a nucleic acid primer bound to the object according to the present invention, if the nucleic acid primer bound object given a label is situated on a flat surface, an aspect in which a step of two-dimensionally imaging the flat surface on which, the object is situated is further provided for the purpose of identifying at least the position of the object on the flat surface is possible. Particularly, if a plurality of objects are situated on different regions on the same flat surface, it is preferable that the regions on which the plurality of objects are situated are identified by two-dimensionally imaging the flat surface on which the objects are situated.

In the method for detecting a single nucleotide polytype of the target nucleic acid according to the present invention, there are cases where after elongation of the nucleic acid strand is carried out, the nucleic acid primer bound object in which a nucleoside having a label substance bound thereto is captured with the elongation of the nucleic acid strand is collected, placed on the flat surface, and detected. If the nucleic acid primer bound object in which a nucleoside having a label substance bound thereto is captured is situated on a flat surface, an aspect in which a step of two-dimensionally imaging the flat surface on which the object is situated is further provided for the purpose of identifying at least the position of the object on the flat surface is possible. Particularly, if a plurality of objects are situated on different regions on the same flat surface, it is preferable that the regions on which the plurality of objects are situated are identified by two-dimensionally imaging the flat surface on which the objects are situated.

If for the nucleic acid primer bound object according to the present embodiment, for example, the label substance and the object itself are detected using various kinds of measurement means described above, or if the nucleic acid primer bound object according to the present embodiment is placed in the form of a flat surface and detected, as a method for placing the object, a method in which a piece of paper is impregnated with a dispersion solution containing the nucleic acid primer bound object and the dispersion solvent is dried when the object is in the form of fine particles, a method in which the object is adsorbed to a flat magnet by a magnetic force when fine particles are magnetic fine particles, or a method described in Science, Vol. 287, 2000, pp. 451-452, for example a method in which a hole having an inner diameter substantially equivalent to the outer diameter of the fine particles is formed on the surface of the front end of a glass fiber using photolithography and the fine particles are buried in the hole may be used.

EXAMPLES

Hereinafter, the present invention will be described in more detail by way of examples. However, those examples are examples of the best modes according to the present invention and the present invention is not limited to modes shown in those examples.

Example 1

Based on a method of producing a ferrite fine particle described in Japanese Patent Application Laid-Open No. 2002-128523, a ferrite fine particle was prepared using a solution containing iron (II) ion as an essential ingredient and to which various metal element ions constituting a ferrite fine particle of interest were added and using an oxidant to oxidize iron (II) ion to iron (III) ion. When the types or added concentrations of the metal element ions to be added in the starting solution were selected in addition to principal ingredient iron ion, the prepared ferrite fine particle had a ferrite-material containing various metal elements in addition to a principal ingredient metal element of iron at a desired content ratio.

In this example, there were prepared: ferrite fine particles to which at least one metal elements selected from a total of 8 metal elements (Co, Ni, Mn, Zn, Cu, Mg, Al, and Ti) were added as minor ingredient metal elements in addition to a principal ingredient metal element (Fe) constituting a ferrite; and a ferrite fine particle to which those 8 types of the metal elements were not added. That is, ferrite fine particles to which at least one metal elements selected from 8 metal elements (Co, Ni, Mn, Zn, Cu, Mg, Al, and Ti) were added were classified into $(2^8-1)$ types=255 types depending on the types of contained metal elements of the 8 metal elements. Further, in combination with a ferrite fine particle to which the 8 metal elements were not added, the prepared ferrite fine particles were classified into a total of 256 types based on the presence or absence of the individual 8 types of the metal elements in the composition.

Note that, in this example, the concentrations of the respective metal, element ions to be added as minor ingredients were regulated to the same level in a solution containing plural metal element ions to be used for preparing ferrite fine particles. The particle size of a finally prepared ferrite fine particle was found to be approximately 500 nm.

The prepared ferrite fine particles were separated from each reaction solution and washed with ultrapure water. Note that, in operations for collecting and separating the ferrite fine particles such as: collection and separation from the reaction solution; and collection after washing, there was used a technique for collecting ferrite particles using a magnet. A total of 256 types of washed ferrite fine particles were separately suspended in ultrapure water, to thereby prepare suspensions each having a dispersion density of about 5.5 mg/mL (about 500 particles/μL).

From the resultant suspensions of ferrite fine particles (total: 256 types), about 1 μl of each suspension was taken and mixed, and then the contained ferrite fine particles were once collected. The fine particles were resuspended in 100 μL of pure water, and 1 μL of the resuspension was spotted on copier paper, followed by drying. Subsequently, the copier paper was appropriately cut off hand the composition of metal elements contained in each ferrite fine particle existing in each spotted portion was measured. In this example, spectra derived from 9 metal elements (Fe, Co, Ni, Mn, Zn, Cu, Mg, Al, and Ti) were measured using a TOF-SIMS apparatus (manufactured by ION-TOF USA, Inc.: TOF-SIMS IV), XPS apparatus (manufactured by JEOL Ltd.: JPS-9200), AES apparatus (manufactured by JEOL Ltd.: JAMP-9500F) while performing two-dimensional imaging of a region including each spotted portion by three measurement methods.

As a result of the two-dimensional imaging, each image of the region in which the ferrite fine particles existed (spotting region) was obtained from each spotting position by any of three measurement methods based on spectra derived from a principal ingredient metal element. At the same time, for spectra derived from minor ingredient metal elements contained in each ferrite fine particle, it was confirmed that spectra unique to at least the individual minor ingredient metal elements (Co, Ni, Mn, Zn, Cu, Mg, Al, and Ti) could be detected without interference due to other ingredient metal elements. That is, it was confirmed that a total of 256 types ($2^8$ types) of ferrite fine particles could be distinguished by selecting eight metal elements (Co, Ni, Mn, Zn, Cu, Mg, Ai, and Ti) as minor ingredient metal elements that could be blended with a principal ingredient metal element (Fe) contained in the ferrite fine particles and by binding a label corresponding to binary system 8-digit numerical value information based on the presence or absence of the eight metal elements.

Next, among the above 256 types of ferrite fine particles, oligonucleotide probes were bound to two types of fine particles labeled with Ni, Mn, Zn, Cu, Mg, Al and Ti and with Co, Mn, Zn, Cu, Mg, Al and Ti, by the following processes.

(1) An appropriate amount of, fine particles was placed into a 0.5 ml-microtube, and 100 μl of ethanol was added thereto. After the resultant mixture was shaken and stirred, ethanol was removed by using a separator utilizing the above magnet and fine particles were collected.

(2) An aqueous solution of 1% by weight of N-β-(aminoethyl)-γ-aminopropyltrimethoxysilane, KBM603 (Shin-Etsu Chemical Co., Ltd.), which is a silane coupling agent having amino acids bound thereto, was stirred at room temperature for two hours to achieve hydrolysis of methoxy group contained in the molecular of the above-mentioned silane compound. Next, the fine particles obtained in the above (1) were immersed into 100 μl of the aqueous solution at room temperature for one hour, and thereafter washed with pure water, collected and dried. Next, the particles were baked for one hour in an oven that was heated to 120° C., and thereby amino acids were eventually introduced onto the surface of the fine particles.

(3) Next, 2.7 mg of N-(6-maleimidecaproyloxy)succinimide (EMCS) was dissolved in a 1:1 mixture solution of dimethylsulfoxide (DMSO) and ethanol so as to have a concentration of 0.3 mg/ml. The fine particles, which had been treated via silane-coupling treatment, were immersed in 100 μl of the EMCS solution at room temperature for two hours to react the amino group, which had been introduced to the substrate surface through the silane coupling treatment, with the succinimide group of EMCS solution. At this stage, maleimide group that was derived from EMCS existed on the particle surface. The substrate was picked up from the EMCS solution, washed sequentially with the mixture solvent of DMSO and ethanol, and then with ethanol, and thereafter, dried under reduced pressure.

(4) The inventors ordered a DNA synthesis company (Bex Co., Ltd.) to synthesize two kinds of single strand nucleic acids each having SEQ ID NOS: 1 and 2. Herein, thiol group (SH) was introduced to the 5' end of each single strand DNA by using thiol modifier (Glenn Research) during the synthesis. Meanwhile, deprotection and DNA recovery were carried out according to conventional methods, and an HPLC was used for purification. The series of all the processes from the synthesis to the purification were conducted by the synthesis company at request of the inventors.

SEQ ID NO: 1
5' HS-(CH2)$_6$-O-PO$_2$-O-ACTGGCCGTCGTTTTACA 3'

SEQ ID NO: 2
5' HS-(CH$_2$)$_6$-O-PO$_2$-O-CGTACGATCGATGTAGCTAGCATGC 3'

(5) The above single strand DNAs were each dissolved into 50 mM phosphate buffer solution (pH=7.0) at a concentration of 8 μM, and the fine particles obtained in the above (3) were immersed in 100 μl of each solution obtained above at room temperature for one hour to react the maleimide group on the fine particle with the thiol group of nucleic acid, so that the nucleic acid as a probe was bound onto the fine particle. Thereafter, the particles were properly washed with the above phosphate buffer solution and preserved in the buffer solution at 4° C. until next use thereof.

These nucleic acid-binding fine particles were properly washed with pure water, collected, and dried under reduced pressure, and then observed with a TOF-SIMS apparatus based on the above-mentioned method. As a result, from two types of ferrite fine particles, each fragment ion of PO$^-$, PO$_2^-$ and PO$_3^-$, of phosphate site of a nucleic acid, and fragment ions of base were strongly observed in addition to atoms as each label. Among the above observed ions, PO$_2^-$ and PO$_3^-$ were particularly strongly observed. Further, the reaction for binding the nucleic acid to the fine particle was caused at various concentrations of nucleic acid, and in the same way, PO$_2^-$ and PO$_3^-$ ions were observed with a TOF-SIMS apparatus. Within a certain range of nucleic acid concentration, ion strength was observed in linear proportion to nucleic acid concentration.

The above indicates that it is possible to distinguish a probe-binding fine particle of the present invention, provided with, an atom as label, from a probe bound to the fine particle, and to detect and identify the probe on the fine particle for relative but quantitative measurement.

Next, as model target nucleic acid, single strand nucleic acids having the base sequence of SEQ ID NOS: 3 and 4 were synthesized so that they have the base sequence complementary to the base sequence of nucleic acid of SEQ ID NOS: 1 and 2, respectively.

Herein, A(Br) represents bromine atom-binding adenylic acid, and this portion was introduced during the synthesis with an automatic synthesizer using 8-bromo-3'-deoxyadenosine phosphoroamidite (Glenn Research) having the structure shown below. Deprotection and DNA recovery were carried out according to conventional methods, and an HPLC was used for purification. The series of all the processes from the synthesis to the purification were conducted by the synthesis company at request of the inventors.

SEQ ID NO: 3
5' TGTA(Br)A(Br)A(Br)A(Br)CGA(Br)CGGCCA(Br)GT 3'

SEQ ID NO: 4
5' GCA(Br)TGCTA(Br)GCTA(Br)CA(Br)TCGA(Br)TCGTA(Br)CG 3'

[Chemical formula 1]

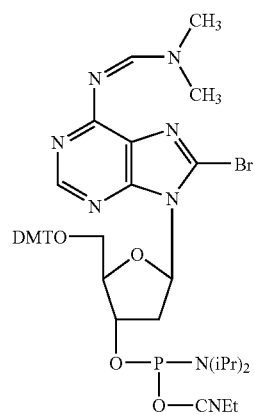

These nucleic acids were each dissolved in 50 mM phosphate buffer solution (pH=7.0) containing 1M NaCl at a concentration of 50 nM, and an appropriate amount of particles having probe nucleic acids of the above SEQ ID NOS: 1 and 2 bound thereto was mixed with and dispersed in 100 μl of the solution. The resultant mixture was allowed to stand at 40° C. for 16 hours for hybridizing the probe nucleic acid on the fine particle with the target nucleic acid. Thereafter, the resultant was washed at room temperature with the above buffer solution and then with pure water. The fine particles were collected and dried under reduced pressure.

Next, the hybridized fine particles were observed with a TOF-SIMS apparatus according to the above method. As a result, from the ferrite fine particles hybridized with corresponding complementary strands, atoms bound to the fine particles as label, the above-mentioned fragment ions that were derived form the nucleic acid probes and target nucleic acids, and Br$^-$ ions derived from the target nucleic acids were observed. Regarding Br$^-$ ion, both $^{79}$Br$^-$, $^{81}$Br$^-$ ions as naturally existing isotope ions were observed with nearly the same ion strength. Further, from the ferrite particles that had been hybridized with noncomplementary nucleic acids, atoms as label and fragment ions derived from nucleic acid probes were observed, but Br$^-$ ions were not observed. Furthermore, the reaction during hybridization was caused at various concentrations of target nucleic acid, and observation was conducted with a TOF-SIMS apparatus. Within a certain range of target nucleic acid concentration, Br$^-$ ion strength was observed in linear proportion to target nucleic acid concentration.

These results show that it is possible to detect, identify, and relatively but quantitatively measure a target nucleic acid specifically bound to (hybridized with) a nucleic acid probe that is bound to a probe-binding fine particle labeled with an atom, of the present invention, using the atom that is contained in the target nucleic acid but not contained in the fine particle or the probe bound to the fine particle.

It should be noted that 256 types of ferrite fine particles mentioned in the present example can have an arbitrary probe bound thereto and can be used for the detection of a target substance specifically bound to the probe.

Example 2

In this Example 2, there were prepared: ferrite fine particles to which one or more metal elements selected from a total of 12 metal elements including eight metal elements (Co, Ni, Mn, Zn, Cu, Mg, Al and Ti) and four metal elements (Ga, Ge, Ag and Pd) were added as minor ingredient metal elements in addition to a principal ingredient metal element (Fe) constituting a ferrite; and a ferrite fine particle to which those 12 types of the metal elements were not added. That is, ferrite fine particles to which at least one metal elements selected from 12 metal elements (Co, Ni, Mn, Zn, Cu, Mg, Al, Ti, Ga, Ge, Ag and Pd) were added were classified into $(2^{12}-1)$ types=4,095 types depending on the types of contained metal elements of the 12 metal elements. Further, in combinations with a ferrite fine particle to which the 12 metal elements were not added, the prepared ferrite fine particles were classified into a total of 4,096 types based on the presence or absence of the individual 12 types of the metal elements in the composition.

Note that, in this example, the concentrations of the respective metal element ions to be added as minor ingredients were regulated to the same level in a solution containing plural metal element ions to be used for preparing ferrite fine particles. However, the contents of the individual 12 metal elements to the content of the principal ingredient metal element (Fe) were lowered to 8/12 of the ratio in Example 1. The particle size of a finally prepared ferrite fine particle was found to be approximately 500 nm.

The prepared ferrite fine particles were separated from each reaction solution and washed with ultrapure water. Note that, in operations for collecting and separating the ferrite fine particles such as: collection and separation from the reaction solution; and collection after washing, there was used a technique for collecting ferrite particles using a magnet. A total of 4,096 types of washed ferrite fine particles were separately suspended in ultrapure water, to thereby prepare suspensions each having a dispersion density of about 5.5 mg/mL (about 500 particles/μL).

From the resultant suspensions of ferrite fine particles (total: 4,096 types), about 1 μl of each suspension was taken and mixed, and then the contained ferrite fine particles were once collected. The fine particles were resuspended in 100 μL of pure water, and 1 μL of the resuspension was spotted on copier paper, followed by drying. Subsequently, the copier paper was appropriately cut off, and the composition of metal elements contained in each ferrite fine particle existing in each spotted portion was measured by the same, measurement procedure and conditions as those of Example 1.

As a result of the two-dimensional imaging for the ferrite fine particles in Example 2, images of regions in which the respective ferrite fine particles exist (spotting regions) may be obtained based on spectrum derived from the principal ingredient metal element from the respective spotting positions by any of the three measurement methods. At the same time, for spectra derived from minor ingredient metal elements contained in each ferrite fine particle, it was confirmed that spectra unique to at least the individual minor ingredient metal elements (Co, Ni, Mn, Zn, Cu, Mg, Al, Ti, Ga, Ge, Ag, and Pd) can be measured without interference due to other ingredient metal elements. That is, it was confirmed that a total of 4,096 types ($2^{12}$ types) of ferrite fine particles could be distinguished by selecting 12 metal elements (Co, Ni, Mn, Zn, Cu, Mg, Al, Ti, Ga, Ge, Ag, and Pd) as minor ingredient metal elements that can be blended for a principal ingredient metal element (Fe) contained in the ferrite fine particles and by binding a label corresponding to binary system 8-digit numerical value information based on the presence or absence of the 12 metal elements.

Those results described above reveal that, when the types number of metal elements that may be selected was further increased as minor ingredient metal elements in addition to a principal ingredient metal element (Fe) constituting a ferrite, the types of labels that may be bound to ferrite fine particles was able to be increased as long as the contents of all of the many metal elements can be evaluated by measuring spectrum unique to the individual metal elements by applying various detection means.

Next, from the above 4,096 types of ferrite fine particles, oligopeptide nucleic acids as probe were bound to two types of fine particles labeled with "Co, Ni, Mn, Zn, Cu, Mg, Al, Ti, Ga, Ge and Ag" and "Ni, Mn, Zn, Cu, Mg, Al, Ti, Ga, Ge, Ag and Pd" in the same manner as in Example 1. Here, thiol group, which was involved in the binding to maleimide group on a fine particle of a probe used for binding, was introduced by binding of cysteine residue having no nucleic acid base at amino terminus (5' end of nucleic acid probe) of the above oligopeptide nucleic acid. The base sequences thereof were the same as SEQ ID NOS: 1 and 2. The synthesis of oligopeptide nucleic acid was conducted by Bex Co., Ltd. at the request of the inventors.

Fine particles having the above oligopeptide nucleic acid probes bound thereto was observed with a TOF-SIMS apparatus. In addition to atoms of fine particles as label, fragments of nucleic acid base derived from oligopeptide nucleic acid probes, were observed. Fragment ions of substances other than oligopeptide nucleic acids were not observed, or distinguishable from fragment ions derived from amino silane coupling agent or EMCS.

Next, the above two types of ferrite particles having the above oligopeptide nucleic acid probes bound thereto were hybridized in the same manner as in Example 1. Here, prepared complementary strands had the same base sequence as SEQ ID NOS: 3 and 4, but no bromine atom was, bound thereto.

After the hybridization, ferrite fine particles were observed with a TOF-SIMS apparatus. Only from ferrite fine particles that had been hybridized with the complementary strands, ions of $PO^-$, $PO_2^-$ and $PO_3^-$ were observed, which were derived from target nucleic acids but not included in fine particles themselves and oligopeptide nucleic acids, in addition to atoms of fine particles as label.

Further, the reaction during hybridization was caused at various concentrations of target nucleic acid, and observation was conducted with a TOF-SIMS apparatus. Within a certain range of nucleic acid concentration, the strengths of $PO_2^-$ and $PO_3^-$ were observed in linear proportion to target nucleic acid concentration.

According to these results, the present invention exhibited usefulness in the case of oligopeptide nucleic acid probe, and no labeled target nucleic acid in the same manner as in Example 1.

It should be noted that 4,096 types ferrite fine particles mentioned in the present example can have an arbitrary probe bound thereto and can be used for the detection of a target substance specifically bound to the probe.

Example 3

In this Example 3, there were prepared: ferrite fine particles to which one or more metal elements selected from eight metal elements (Co, Ni, Mn, Zn, Cu, Mg, Al, and Ti) were added in addition to a principal ingredient metal element (Fe) constituting a ferrite; and a ferrite fine particle to which those eight types of the metal elements were not added. Note that, in Example 3, in a solution containing plural types of metal element ions to be used for preparing ferrite fine particles, two levels of the concentration same as that in Example 1 and 1/10 thereof were used for two types (Ni and Zn) with respect to the concentrations of the respective metal element ions to be added as minor ingredients.

That is, the ferrite fine particles to which one or more types of metal element selected from eight metal elements (Co, Ni, Mn, Zn, Cu, Mg, Al, and Ti) were added were classified into ($2^6 \times 3^2 - 1$) types=575 types based on: the contained metal element types of six metal elements (Co, Mn, Cu, Mg, Al, and Ti) (the number of occurrences $2^6$); and differences of the level of contents for two types (Ni and Zn) (the respective three levels: 0, 1/10, and 1) (the number of occurrences $3^2$). Further, in combination with a ferrite fine particle to which the eight metal elements were not added, the prepared ferrite fine particles were classified into a total of 576 types ($2^6 \times 3^2$ types) based on the level of contents of the individual eight types of the metal elements in the composition. Note that, in this example, the particle size of a finally prepared ferrite fine particle was found to be approximately 500 nm.

From the resultant suspensions of ferrite fine particles (total: 575 types), about 1 μl of each suspension was taken, and then the suspension was spotted on copier, paper, followed by drying. Subsequently, the copier paper was appropriately cut off by the same measurement procedure, and condition as those of Example 1, and the composition of the metal elements contained in the ferrite fine particles existing in each spotted portion was measured.

As a result of the two-dimensional imaging for the ferrite fine particles of Example 3, there were obtained images of the respective regions in which the ferrite fine particles existed (spotting position) from the respective spotting position based on spectra derived from the principal ingredient metal element in any of the three measurement procedures. At that time, for spectra derived from the minor ingredient metal elements contained in each ferrite fine particle, there were confirmed that spectra unique to at least minor ingredient metal elements (Co, Ni, Mn, Zn, Cu, Mg, Al, Ti, Ga, Ge, Ag and Pd) could be measured without interference due to other ingredient metal elements and that differences in the level of contents of two types (Ni and Zn) could clearly be distinguished. That is, it was confirmed that a total of 576 types ($2^6 \times 3^2$ types) of ferrite fine particles could be distinguished by selecting eight metal elements (Co, Ni, Mn, Zn, Cu, Mg, Al and Ti) as minor ingredient metal elements that may be blended for a principal ingredient metal element (Fe) contained in a ferrite fine particle and binding labels corresponding to more than binary system 8-digit numerical value information, e.g., labels corresponding to binary system 6-digit and ternary 2-digit numerical value information based on differences in the level of contents of the eight metal elements.

The above-described results reveal that, for types number (n) of metal elements that may be selected as minor ingredient metal elements in addition to a principal ingredient metal element (iron) constituting ferrite, labels corresponding to, e.g., M-ary system n-digit numerical value information can be bound to ferrite fine particles as long as not only the presence or absence but also plural of level of contents (level number M) of all of the n-metal elements can be evaluated by measuring spectra unique to individual metal elements by applying various detection means. Next, among the above 576 types of ferrite particles, nucleic acid probes were bound to the total of three types of fine particles with three different concentration levels (no-containing, the same concentration as Example 1 and 1/10 thereof) of Ni atom of eight atoms (Co, Ni, Mn, Zn, Cu, Mg, Al and Ti), by the following method.

(1) According to the completely same method as in Example 1, the fine particles were treated with aminosilane coupling agent and EMCS to introduce a maleimide group onto the surface of a fine particle.

(2) An aqueous solution of 0.5 mg/ml 1-thioglycerol (Sigma-Aldrich) was prepared, and an appropriate amount of each of the above three types of ferrite fine particles was immersed in 100 μl of the solution to introduce a hydroxyl group onto the fine particle surface.

(3) Nucleic acids having the following SEQ ID NO: 5, in addition to the above SEQ ID NOS: 1 and 2, as probe nucleic acids, were sequentially synthesized, by an automatic nucleic acid synthesizer, with the three types of ferrite fine particles having the above hydroxyl group introduced thereto.

SEQ ID NO: 5
5' HS-(CH$_2$)$_6$-O-PO$_2$-O-TTTTTTTTTTTTTTTTTTTTTTTTTTTT 3'

The synthesis was conducted by Bex Co., Ltd. at request of the inventors. The protocols for the synthesis were all conducted according to conventional methods.

The fine particles having these three types of nucleic acids bound thereto were observed with a TOF-SIMS apparatus. As a result of that, it was possible to detect each atom as label including the three levels in the three types of ferrite fine particles. In addition, each fragment ion of PO$^-$, PO$_2^-$ and PO$_3^-$, of phosphate site of a nucleic acid, and fragment ions of base were strongly observed. From fine particles having probes of SEQ ID NO: 5 bound thereto, fragment ions derived from thymine were observed as base-derived fragment ions. Among the above ions, PO$_2^-$ and PO$_3^-$ were particularly strongly observed.

The above shows that it is possible to distinguish a probe binding fine particle labeled with atoms including an atom existing at three levels, from a probe bound to the fine particle by solid phase sequential synthesis; and to detect and identify the probe on fine particle.

Next, hybridization to the three types of ferrite particles with the above nucleic acid probes bound thereto was carried out in the same manner as in Example 1. Prepared complementary strands are the following SEQ ID NO: 6 complementary to SEQ ID NO: 5, in addition to SEQ ID NOS: 3 and 4.

SEQ ID NO: 6
5' A(Br)A(Br)A(Br)A(Br)A(Br)AAAAAAAAAAAAAAAAAAAA AAAAA 3'

Here, 5 bases at 5' end side of SEQ ID NO: 6 had bromine atoms bound thereto in the same manner as SEQ ID NOS: 3 and 4.

Next, fine particles that were subjected to hybridization, were observed with a TOF-SIMS apparatus based on the above-mentioned method. As a result of that, from the ferrite fine particles that were hybridized with the complementary strands, atoms bound to the fine particles as labels, including three levels of Ni atom, were detectable. Further, the fragment ions derived from nucleic acid probes and target nucleic acid, and $^{79}$Br$^-$ and $^{81}$Br$^-$ ions derived from target nucleic acid were observed. Further, from the ferrite particles that were subjected to hybridization with noncomplementary nucleic acid, atoms as labels and fragment ions derived from nucleic acid probe were observed, but $^{79}Br^-$ and $^{81}Br^-$ ions were not observed.

Furthermore, the reaction was caused at various concentrations of target nucleic acid during hybridization, and observation was conducted with a TOF-SIMS apparatus. Within a certain range of nucleic acid concentration, $^{79}Br^-$ and $^{81}Br^-$ ion strengths were observed in linear proportion to target nucleic acid concentration.

These results show that it is possible to detect, identify and relatively but quantitatively measure a target nucleic acid specifically bound to (hybridized with) a nucleic acid probe that is bound, by solid phase sequential synthesis, to a probe-binding fine particle labeled with an atom, of the present invention, using the atom that is contained in the target nucleic acid but not contained in the fine particle or the probe bound to the fine particle.

It should be noted that 575 types of ferrite fine particles mentioned in the present example can have an arbitrary probe bound thereto and can be used for the detection of a target substance specifically bound to the probe.

Example 4

Nature Biotechnology Vol. 18, 438, 2000 describes preparation of an oligonucleotide chip for detecting the mutation in exon 7 of the genome DNA of two cell lines HSC4 and HSC5 of human oral squamous carcinoma, and detection of fluorescence labeled nucleic acid derived from the exon. In this example, ferrite fine particles having oligonucleotide probes bound thereto were prepared according to the above method; a target nucleic acid was synthesized using bromine in place of a fluorescent label; and further hybridization was performed using the target nucleic acid.

A specific procedure thereof is described below.

```
                                              SEQ ID NO: 7
5' HS-(CH2)6-O-PO2-O-GATGGGCCTCCGGTTCAT 3'

SEQ ID NO: 8
5' HS-(CH2)6-O-PO2-O-GATGGGCCACCGGTTCAT 3'

SEQ ID NO: 9
5' HS-(CH2)6-O-PO2-O-GATCGGCCACCGGATCAT 3'
```

A single strand nucleic acid of SEQ ID NO: 7, having a base sequence complementary to a part of the base sequence of the above exon 7 of HSC4 (a part containing codon No. 248) and carrying a thiol group at the 5' end for binding to the substrate, was synthesized in the same manner as in Example 1. In addition, though SEQ ID NO: 7 is completely complementary, single strand nucleic acids having single and triple base mismatch sites (underlined nucleotides) to the target base sequence were synthesized (SEQ ID NOS: 8 and 9, respectively).

From 256 types of ferrite fine particles labeled with the group of atoms comprising Co, Ni, Mn, Zn, Cu, Mg, Al and Ti in Example 1, fine particles labeled with "Ni, Mn, Zn, Cu, Mg, Al and Ti", "Co, Ni, Mn, Zn, Cu, Mg and Al" and "Co, Ni, Mn, Cu, Mg, Al and Ti" were selected, and single strand nucleic acids of SEQ ID NOS: 7, 8 and 9 were bound to the fine particles, respectively, in the same manner as in Example 1. The methods of Example 1 were performed to distinguish among the prepared probe-binding ferrite fine particles and to confirm bound probes.

```
                                              SEQ ID NO: 10
E7S: 5'- ACTGGCCTCATCTTGGGCCT- 3'   (exon 7, sense)

SEQ ID NO: 11
E7A: 5'- TGTGCAGGGTGGCAAGTGGC- 3'   (exon 7, anti-
                                     sense)
```

[Chemical formula 2]

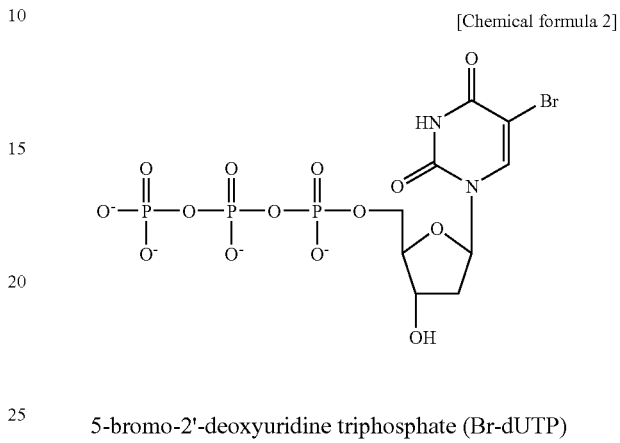

5-bromo-2'-deoxyuridine triphosphate (Br-dUTP)

Next, an exon 7 portion from the genome of HSC4 was amplified by PCR reaction using. PCR primers of the above SEQ ID NOS: 10 and 11 (the synthesis thereof was ordered to Bex Co., Ltd.). That is, 50 µl of PCR mixture containing 20 ng of genome DNA, 0.4 µM of sense primers and 0.4 µM of anti-sense primers, was subjected to 40 cycles of PCR amplification, each cycle consisting of 30 seconds at 94° C. and 45 seconds at 60° C. The obtained product was designed to have a chain length of 171 nucleotides.

Subsequently, using a part of the above amplified product as a template, 0.2 µM of sense primers (SEQ ID NO: 10); and 5-bromo-2'-deoxyuridine triphosphate (Sigma-Aldrich), as a kind of the bromine labeled nucleotide having the structure shown above, were added to 10 µM of 2'-deoxyuridine triphosphate at 1/10 concentration of the ordinary one, and subjected to ssPCR (single strand PCR). PCR was carried out by repeating 25 cycles of 30 seconds at 96° C., 30 seconds at 50° C., and 4 minutes at 60° C. Here, other three types of deoxynucleotide triphosphate were all used at a concentration of 10 µM. Further, the obtained bromine labeled single strand DNA was purified by gel filtration.

Using the three types of nucleic acid probe-binding ferrite fine particle chips and the above ssPCR product, hybridization was carried out in the same method as in Example 1. The ssPCR product had a concentration of 10 nM, and 6×SSPE (0.9M NaCl, 60 mM NaH$_2$PO$_4$, 6 mM EDTA) containing 20% of formamide was used as a buffer solution. The above chip and product were heated at 80° C. for 10 minutes; hybridized at 45° C. for 15 hours; and thereafter washed at 55° C. using 2×SSPE. Next, they were properly washed with pure water (room temperature), and ferrite particles were collected and dried under reduced pressure.

The obtained ferrite fine particles were observed with a TOF-SIMS apparatus. From fine particles having bound thereto nucleic acid probes completely complementary to a target base sequence part of a target nucleic acid, $^{79}Br^-$ and $^{81}Br^-$ ions were observed with strong ion intensity. Next, from fine particles having bound thereto nucleic acid probes with single base mismatch, $^{79}Br^-$ and $^{81}Br^-$ ions were observed with about 1/10 of ion intensity of the above fullmatch case. From fine particles having bound thereto nucleic acid probes with triple base mismatch, $^{79}Br^-$ and $^{81}Br^-$ ions were not observed.

These results show that the probe-binding fine particle of the present invention enables the detection of a gene derived from actual cell genome by identifying a single base mismatch, together with a labeling method wherein a label is incorporated into a target nucleic acid during PCR.

It should be noted that 256 types of ferrite fine particles mentioned in this example can have an arbitrary probe bound thereto and can be used for the detection of a target substance specifically bound to the probe.

Example 5

```
                                    SEQ ID NO: 12
E7S:  5'- A(Br)CTGGCCTCA(Br)TCTTGGGCCT- 3' (exon 7,
                                            sense)
```

Instead of incorporated label in Example 4, a single strand nucleic acid of the above SEQ ID NO: 12 (base sequence is the same as SEQ ID NO: 10) that has been labeled with bromine in the same manner as a bromine labeled model target nucleic acid of Example 1 was used to label a target nucleic acid.

Hybridization and TOF-SIMS observation were carried out in the same manner as in Example 4. As a result, though the ion intensity was generally low compared with that of Example 4, but the results exhibited the same tendency as Example 4.

These results show that the probe-binding fine particle of the present invention enables the detection of a gene derived from actual cell genome by identifying a single base mismatch, together with a labeling method wherein a target nucleic acid is labeled with a primer during PCR.

Example 6

Primer Basic Case Example 1

In the same manner as in Example 1, 256 types of ferrite fine particles were prepared. Among them, two types, A particle and B particle labeled with "Ni, Mn, Zn, Cu, Mg, Al and Ti" and "Co, Mn, Zn, Cu, Mg, Al and Ti", respectively were treated in the following processes to have oligonucleotide primers bound to the surface thereof.

Step (1): Ethanol Washing

A proper amount of fine particles was place in a 0.5 ml-microtube, and 100 μl of ethanol was added thereto. After the resultant-mixture was shaken and stirred, ethanol was removed by using a separator utilizing the above magnet and fine particles were collected.

Step (2): Introduction of Amino Group

An aqueous solution of 1% by weight of N-(β-aminoethyl)-γ-aminopropyltrimethoxysilane, KBM603 (Shin-Etsu Chemical Co., Ltd.), which is a silane coupling agent having amino acids bound thereto, was stirred at room temperature for two hours to achieve hydrolysis of methoxy group contained in the molecular of the above-mentioned silane compound. Next, the fine particles obtained in the above (1) were immersed into 100 μl of the aqueous solution at room temperature for one hour, and thereafter washed with pure water, collected and dried. Next, the particles were baked for one hour in an oven that was heated to 120° C., and thereby amino groups were eventually introduced onto the surface of the fine particles which had been treated with the silane coupling agent.

Step (3): Introduction of Maleimide Group Via a Linker

Next, 2.7 mg of N-(6-maleimidecaproyloxy)succimide (EMCS) was dissolved in a 1:1 mixture solvent of dimethylsulfoxide (DMSO) and ethanol so as to have a concentration of 0.3 mg/ml. The fine particles, which had been treated with the silane coupling agent, were immersed in 100 μl of the EMCS solution at room temperature for two hours to react the amino group, which has been introduced to the particle surface through the silane coupling treatment, with the succinimide ester group of EMCS. As a result of this reaction, amide bond (—CO—NH—) was formed, and the fine particle surface had a maleimide group derived from EMCS introduced thereon via a linker (—(CH$_2$)$_5$—CO—NH—). The fine particles were pulled out of EMCS solution; washed with the above DMSO/ethanol mixture solvent and ethanol sequentially; and thereafter dried under reduced pressure.

Step (4): Preparation of a Single Strand DNA for Nucleic Acid Primer

Synthesis of two types of single, strand DNA molecules each having SEQ ID NOS: 1 and 2 was ordered to a DNA synthesis company (Bex Co., Ltd.). During the synthesis, a sulfanil group (—SH) was introduced to the 5' end of each single strand DNA by using thiol modifier (Glen Research). Meanwhile, deprotection and DNA recovery were carried out according to conventional methods, and an HPLC was used for purification.

```
                                    SEQ ID NO: 13
    5' HS—(CH₂)₆—O—PO₂—O-TGTAAAACGACGGCCAGT 3'

SEQ ID NO: 14
    5' HS—(CH₂)₆—O—PO₂—O-TGTAAAACGACGGCCAGA 3'
```

SEQ ID NO: 13 is a base sequence completely complementary to a partial base sequence (from 6,290th nucleotide to 6,307th nucleotide) of a commercially available single strand nucleic acid molecule M13mp18 (Sigma-Aldrich). SEQ ID NO: 14 is a base sequence wherein the 3' end of SEQ ID NO: 13 was mutated from T to A.

Step (5): Binding of Nucleic Acid Primer to Fine Particle Surface

The above two types of single strand DNAs were each dissolved into 50 mM phosphate buffer solution (pH 7.0) at a concentration of 8 μM, so that two types of solutions were prepared. The fine particles prepared in the above (3), having a maleimide group introduced on the surface, were immersed in 100 μl of each solution at room temperature for one hour to react the maleimide group on the fine particle surface with the sulfanil group (—SH) at 5' end of single strand DNA. By the reaction between these two functional groups, the single strand DNA was bound at its 5' end to the fine particle surface via a linker. Thereafter, fine particles having single strand DNAs bound thereto were collected from single strand DNA solution, and the remaining single strand DNA solution was properly washed and removed with phosphate buffer solution. After the washing, the fine particles with single strand DNAs bound thereto were dispersed in a phosphate buffer solution and preserved therein at 4° C. until the next use.

Here, DNA primers of SEQ ID NOS: 13 and 14 were bound to the surface of A and B particles, respectively.

The nucleic acid primer-binding fine particles were properly washed with pure water, collected, and dried under reduced pressure, and then observed with a TOF-SIMS apparatus based on the above-mentioned method. As a result, from two types of ferrite fine particles, each fragment ion of PO⁻, $PO_2^-$ and $PO_3^-$, of phosphate site of a single strand nucleic acid, and fragment ions of base were strongly observed in addition to atoms as each label. Among the above observed fragment ions derived from the single strand nucleic acid, $PO_2^-$ and $PO_3^-$ were particularly strongly observed. Further, the concentration of nucleic acid in the single strand DNA solution was varied in the range of 0.05 µM to 150 µM during the binding reaction of a single strand nucleic acid to the fine particle surface, and thereby nucleic acid primer-binding particles having different area densities of single strand DNA bound to the surface were prepared. These nucleic acid primer-binding particles having different area densities of single strand DNA bound to the surface were observed with a TOF-SIMS in the same way in terms of $PO_2^-$ and $PO_3^-$ ions derived from single strand nucleic acid. When the nucleic acid concentration in the single strand DNA solution was 0.15 µM to 40 µM, ion intensity was observed in linear proportion to nucleic acid concentration.

Regarding the nucleic acid primer-binding fine particle labeled with an atom of the present invention, the above results verify that it is possible to identify a label bound to the fine particle, and based on that, to distinguish the types of nucleic acid primer bound to the fine particle surface. Further, they verify that it is possible to detect a nucleic acid primer using a fragment ion derived from the nucleic acid primer as an index, in a state wherein the primer is bound to the fine particle surface. Furthermore, they verify that it is possible to relatively but quantitatively measure the amount (area density) of nucleic acid primer bound to the fine particle surface.

Next, using the nucleic acid primer bound to the above fine particle, elongation reaction of nucleotide to the 3' end of nucleic acid primer was carried out by using a single strand nucleic acid M13mp18 of model target nucleic acid as a template.

[Chemical formula 2]

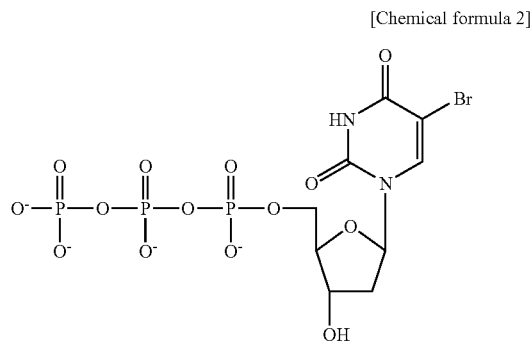

5-bromo-2'-deoxyuridine triphosphate (Br-dUTP)

Regarding the above two types of nucleic acid-primer binding fine particles, 50 µl of PCR mixture containing 100 ng of M13mp18 DNA (Sigma-Aldrich), a proper amount of each nucleic acid primer-binding fine particle, and four kinds of deoxynucleotide triphosphate (Sigma-Aldrich: 10 µM each), was subjected to elongation reaction (ssPCR: single strand PCR), using a commercially available PCR amplification kit, by repeating 25 temperature cycles of 30 seconds at 96° C.; 30 seconds at 50° C.; and 4 minutes at 60° C. Usually; deoxynucleotide triphosphate of adenine, guanine, cytosine and thymine is used, but herein, instead of deoxynucleotide triphosphate of thymine, 2'-deoxyuridine triphosphate was used. Further, as deoxynucleotide triphosphate having a label substance bound thereto, 5-bromo-2'-deoxyuridine triphosphate (Sigma-Aldrich) as a kind of bromine labeled nucleotide, was added to 2'-deoxyuridine triphosphate at ¹⁄₁₀ concentration thereof.

After the elongation reaction, ferrite fine particles in each reaction solution were properly washed with pure water; collected; and dried under reduced pressure. Thereafter, ions derived from label substance (Br) in deoxynucleotide triphosphate with the label substance bound thereto were observed with a TOF-SIMS apparatus by the above-mentioned method. From A particle, bromine ions ($^{79}Br^-$ and $^{81}Br^-$ ions) derived from the above Br-dUTP, which was introduced by the elongation reaction, were detected, in addition to each atomic ion contained as a label. On the other hand, from B particle, each atomic ion contained as a label was detected, but bromine ions were not detected. That is, the single strand DNA of SEQ ID NO: 14 bound to the surface of B particle had different single nucleotide at its 3' end and thus base pairs with template were not formed. This confirms that no elongation reaction to 3' end occurred.

The results of this example mentioned above, verify that it is possible to detect a single nucleotide polymorphism existing in target nucleic acid by applying the method for detecting a single nucleotide polymorphism of a target nucleic acid according to the first embodiment of the present invention.

Example 7

In this Example 71, there were prepared: ferrite fine particles to which one or more metal elements selected from a total of 12 metal elements including eight metal elements (Co, Ni, Mn, Zn, Cu, Mg, Al and Ti) and four metal elements (Ga, Ge, Ag and Pd) were added as minor ingredient metal elements in addition to a principal ingredient metal element (Fe) constituting a ferrite; and a ferrite fine particle to which those 12 types of the metal elements were not added. That is, ferrite fine particles to which one or more metal elements selected from 12 metal elements (Co, Ni, Mn, Zn, Cu, Mg, Al, Ti, Ga, Ge, Ag and Pd) were added were classified into ($2^{12}$−1) types=4,095 types depending on the types of contained metal elements of the 12 metal elements. Further, in combination with a ferrite fine particle to which the 12 metal elements were not added, the prepared ferrite fine particles were classified into a total of 4,096 types based on the presence or absence of the individual 12 types of the metal elements in the composition.

Note that, in this example, the concentrations of the respective metal element ions to be added as minor ingredients were regulated to the same level in a solution containing plural metal element ions to be used for preparing ferrite fine particles. However, the contents of the individual 12 metal elements to the content of the principal ingredient metal element (Fe) was lowered to ⁸⁄₁₂ of the ratio in Example 1. The particle size of a finally prepared ferrite fine particle was found to be approximately 500 mm.

The prepared ferrite fine particles were separated from each reaction solution and washed with ultrapure water. Note that, in operations for collecting and separating the ferrite fine particles such as: collection and separation from the reaction solution; and collection after washing, there was used a technique for collecting ferrite particles using a magnet. A total of 4,096 types of washed ferrite fine particles were separately suspended in ultrapure water, to thereby prepare suspensions each having a dispersion density of about 5.5 mg/mL (about 500 particles/µL).

From the resultant suspensions of ferrite fine particles (total: 4,096 types), about 1 µl of each suspension was taken and mixed, and then the contained ferrite fine particles were once collected. The fine particles were resuspended in 100 μL of pure water, and 1 μL of the resuspension was spotted on copier paper, followed by drying. Subsequently, the copier paper was appropriately cut off, and the composition of metal elements contained in each ferrite fine particle existing in each spotted portion was measured by the same measurement procedure and conditions as those of Example 1.

As a result of the two-dimensional imaging for the ferrite fine particles in Example 7, images of regions in which the respective ferrite fine particles exist (spotting regions) may be obtained based on spectrum derived from the principal ingredient metal element from the respective spotting positions. At the same time, for spectra derived from minor ingredient metal elements contained in each ferrite fine particle, it was confirmed that spectra unique to at least the individual minor ingredient metal elements (Co, Ni, Mn, Zn, Cu, Mg, Al, Ti, Ga, Ge, Ag and Pd) can be detected without interference due to other ingredient metal elements. That is, it was confirmed that a total of 4,096 types ($2^{12}$ types) of ferrite fine particles can be distinguished by selecting 12 metal elements (Co, Ni, Mn, Zn, Cu, Mg, Al, Ti, Ga, Ge, Ag and Pd) as minor ingredient metal elements that can be blended for a principal ingredient metal element (Fe) contained in the ferrite fine particles and by binding a label corresponding to binary system 8-digit numerical value information based on the presence or absence of the 12 metal elements.

Those results described above reveal that, when the number of types of metal elements that may be selected is further increased as minor ingredient metal elements in addition to a principal ingredient metal element (Fe) constituting a ferrite, the types of labels that may be bound to ferrite fine particles can be increased as long as the contents, of all of the many metal elements can be evaluated by measuring spectrum unique to the individual metal elements by applying various detection means.

Next, in this example, among the above 4,096 types of ferrite fine particles, two types of particles C and D, labeled with "Co, Ni, Mn, Zn, Cu, Mg, Al, Ti, Ga, Ge and Ag" and "Ni, Mn, Zn, Cu, Mg, Al, Ti, Ga, Ge, Ag and Pd", respectively, were treated with γ-glycidoxypropyltrimethoxysilane KBM403 (Shin-Etsu Chemical Co., Ltd.) as a silane coupling agent having an epoxy group to introduce a glycidyl group (2,3-epoxypropyl group) thereinto. The conditions for this treatment with silane coupling agent were the same as in Example 3. Ferrite fine particles having glycidyl group (2,3-epoxypropyl group) introduced on the surface, were washed with pure water, collected, and dried under reduced pressure.

On the other hand, single strand DNAs of the following SEQ ID NOS: 15 and 16, wherein sulfanil group (—SH) has been introduced to 5' end as a nucleic acid primer to be bound to each particle surface, were sequentially synthesized with an automatic nucleic acid synthesizer. Deprotection, purification, etc. are carried out according to the ordinary synthesis protocols.

```
                                              SEQ ID NO: 15
5' HS-(CH2)6-O-PO2-O-TGTAAAACGACGGCCAG 3'

SEQ ID NO: 16
5' HS-(CH2)6-O-PO2-O-TGTAAAACGACGGCCAC 3'
```

Here, SEQ ID NO: 15 is a base sequence completely complementary to the base sequence from 6,291th nucleotide to 6,307th nucleotide of single strand nucleic acid M13mp18, and SEQ ID NO: 16 is a base sequence wherein its 3' end of SEQ ID NO: 15 is mutated from G to C. DNA primers of SEQ ID NOS: 15 and 16 were bound to the surface of C and D particles, respectively, through reaction between glycidyl group (2,3-epoxypropyl group) and sulfanil group (—SH).

The prepared two types of nucleic acid primer-binding fine particles were observed with a TOF-SIMS apparatus in the same manner as in Example 1. From each of the two types of fine particles, each fragment ion of $PO^-$, $PO_2^-$ and $PO_3^-$, of phosphate site of a single strand DNA, and fragment ions of base were strongly observed, in addition to each atom contained as label. Among the observed fragment ions derived from single strand DNA, $PO_2^-$ and $PO_3^-$ were particularly strongly observed.

It should be noted that 4,096 types of ferrite fine particles mentioned in this example can have an arbitrary nucleic acid primer bound thereto and can be used to detect a target substance specifically bound to the nucleic acid primer.

Next, using the nucleic acid primer bound to the above fine particle, single nucleotide elongation reaction was carried out to 3' end of the nucleic acid primer by using a single strand nucleic acid. M13mp18 of model target nucleic acid as template.

[Chemical formula 2]

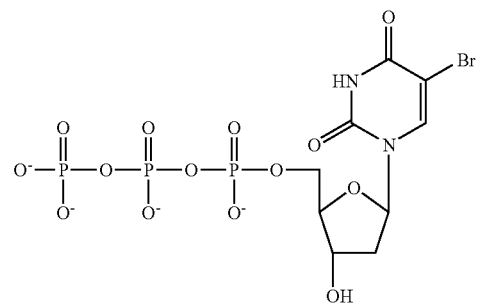

5-bromo-2',3'-dideoxyuridine triphosphate
(Br-ddUTP)

Regarding the above two types of nucleic acid-primer binding fine particles, 50 μl of PCR mixture containing 100 ng of M13mp18 DNA (Sigma-Aldrich), a proper amount of each nucleic acid primer-binding fine particle, and 5-bromo-2',3'-dideoxyuridine triphosphate (Br-ddUTP: 10 μM) as dideoxyuridine triphosphate having a label substance bound thereto, was subjected to elongation reaction (ssPCR: single strand PCR), using a commercially available PCR amplification kit, by repeating 25 temperature cycles of 30 seconds at 96° C.; 30 seconds at 50° C.; and 4 minutes at 60° C.

After the elongation reaction, ferrite fine particles in each reaction solution were properly washed with pure water; collected; and dried under reduced pressure. Thereafter, ions derived from label substance (Br) in dideoxynucleotide triphosphate with the label substance bound thereto were observed with a TOF-SIMS apparatus by the above-mentioned method. From C particle, bromine ions ($^{79}Br^-$ and $^{81}Br^-$ ions) derived from the above Br-ddUTP, which was introduced by the elongation reaction, were detected, in addition to each atomic ion contained as a label. On the other hand, from D particle, each atomic ion contained as a label was detected, but bromine ions were not detected. That is, the single strand DNA of SEQ ID NO: 14 bound to the surface of D particle had different single nucleotide at its 3' end and thus base pairs with template were not formed. As a result, it is confirmed that no elongation reaction to the 3' end occurred.

The results of this example mentioned above, verify that it is possible to detect a single nucleotide polymorphism existing in target nucleic acid by applying the method for detecting a single nucleotide polymorphism of a target nucleic acid according to the second embodiment of the present invention.

Example 8

In this Example 8, there were prepared: ferrite fine particles to which one or more metal elements selected from eight metal elements (Co, Ni, Mn, Zn, Cu, Mg, Al and Ti) were added in addition to a principal ingredient metal element (Fe) constituting a ferrite; and a ferrite fine particle to which those eight types of the metal elements were not added. Note that, in Example 8, in a solution containing plural types of metal element ions to be used for preparing ferrite fine particles, two levels of the concentration same as that in Example 1 and 1/10 thereof were used for two types (Ni and Zn) with respect to the concentrations of the respective metal element ions to be added as minor ingredients.

That is, the ferrite fine particles to which one or more types of metal elements selected from eight metal elements (Co, Ni, Mn, Zn, Cu, Mg, Al, and Ti) were added were classified into ($2^6 \times 3^2 - 1$) types=575 types based on: the contained metal element types of six metal elements (Co, Mn, Cu, Mg, Al and Ti) (the number of occurrences $2^6$); and differences of the level of contents for two types (Ni and Zn) (the respective three levels: 0, 1/10, and 1) (the number of occurrences $3^2$). Further, in combination with a ferrite fine particle to which the eight metal elements were not added, the prepared ferrite fine particles were classified into a total of 576 types ($2^6 \times 3^2$ types) based on the level of contents of the individual eight types of the metal elements in the composition. Note that, in this example, the particle size of a finally prepared ferrite fine particle was found to be approximately 500 nm.

From the resultant suspensions of ferrite fine particles (total: 575 types), about 1 μl of each suspension was taken, and then the suspension was spotted on copier paper, followed by drying. Subsequently, the copier paper was appropriately cut off by the same measurement procedure and condition as those of Example 1, and the composition of the metal elements contained in the ferrite fine particles existing in each spotted portion was measured.

As a result of the two-dimensional imaging for the ferrite fine particles of Example 8, there were obtained images of the respective regions in which the ferrite fine particles existed (spotting position) from the respective spotting position based on spectra derived from the principal ingredient metal element in any of the three measurement procedures. At that time, for spectra derived from the minor ingredient metal elements contained in each ferrite fine particle, it was confirmed that spectra unique to at least minor ingredient metal elements (Co, Ni, Mn, Zn, Cu, Mg, Al, Ti, Ga, Ge, Ag and Pd) can be measured and that differences in the level of contents of two types (Ni and Zn) can clearly be distinguished. That is, it was confirmed that a total of 576 types ($2^6 \times 3^2$ types) of ferrite fine particles can be distinguished by selecting eight metal elements (Co, Ni, Mn, Zn, Cu, Mg, Al and Ti) as minor ingredient metal elements that may be blended for a principal ingredient metal element (Fe) contained in a ferrite fine particle and binding labels corresponding to more than binary system 8-digit numerical value information, e.g., labels corresponding to binary system 6-digit and ternary system 2-digit numerical value information based on differences in the level of contents of the eight metal elements.

The above-described results reveal that, for types number (n) of metal elements that may be selected as minor ingredient metal elements in addition to a principal ingredient metal element (iron), labels corresponding to, e.g., M-ary system n-digit numerical value information can be bound to ferrite fine particles as long as not only the presence or absence but also plural of level of contents (level number M) of all of the n-metal elements can be evaluated by measuring spectra unique to individual metal elements by applying various detection means.

Next, among the above 576 types of ferrite fine particles, nucleic acid primers were bound to the total of three types of fine particles with three different concentration levels (no-containing, the same concentration as Example 1 and 1/10 thereof) of Ni atom of eight atoms (Co, Ni, Mn, Zn, Cu, Mg, Al and Ti), by the following method.

According to the completely same method as in Example 1, the treatment with amino silane coupling agent and EMCS was conducted so that a maleimide group was introduced onto the surface of a fine particle. Further, an aqueous solution of 0.5 mg/ml 1-thioglycerol (Sigma-Aldrich) was prepared, and, an appropriate amount of each of the above three types of ferrite fine particles was immersed in 100 μl of the solution to introduce a hydroxyl group onto the fine particle surface.

To the hydroxyl groups introduced onto the surface of the above three types of ferrite fine particles, nucleic acid strands were sequentially synthesized with an automatic nucleic acid synthesizer, and prepared were nucleic acid primer-binding fine particles, to the surface of which a single strand DNA with the following base sequence was bound at 5' end thereof.

| | |
|---|---|
| 5' TGTAAAACGACGGCCAGT 3' | SEQ ID NO: 13 |
| 5' TGTAAAACGACGGCCAGA 3' | SEQ ID NO: 14 |
| 5' TTTTTTTTTTTTTTTTTTTTTTTTTTTTTT 3' | SEQ ID NO: 17 |

Here, as mentioned in Example 1, SEQ ID NO: 13 is a base sequence completely complementary to a partial base sequence from 6,290th nucleotide to 6,307th nucleotide of commercially available single strand nucleic acid molecule M13mp18 (Sigma-Aldrich), and SEQ ID NO: 14 is a base sequence having a mutation from T to A at the 3' end of SEQ ID NO: 13. Further, SEQ ID NO: 17 corresponds to a poly T sequence hybridizable with a poly A sequence.

The prepared three types of nucleic acid primer-binding fine particles were observed with a TOF-SIMS apparatus in the same manner as in Example 1. From each of the three types of fine particles, each atom contained as label was detected, and in particular, regarding Ni atom, three levels of ion intensities were detected, corresponding to the difference of concentration of its content. In addition, each fragment ion of $PO^-$, $PO_2^-$ and $PO_3^-$, of phosphate site of a single strand DNA, and fragment ions of base were strongly observed. From fine particles shaving the nucleic acid primer of SEQ ID NO: 17 bound thereto, only fragment ions derived from thymine as base-derived fragment ion were observed. For all the three types of nucleic acid primer-binding fine particles, $PO_2^-$ and $PO_3^-$ were particularly strongly observed among the observed fragment ions derived from single strand DNA.

The above results verify that, regarding the nucleic acid primer-binding fine particle labeled with an atom, it is possible to identify the label bound to the fine particle, and based on that, to distinguish the types of nucleic acid primer bound to the fine particle surface. Particularly, in terms of the concentration of contained atom as a label bound to the fine particle, it is confirmed that concentration level of the contained atom can be identified with sufficiently high accuracy by setting definitely distinguishable three levels of the concentration. Further, using a fragment ion derived from the nucleic acid primer as an index, it is possible to detect the nucleic acid primer in a state wherein the primer is bound to the fine particle surface. Furthermore, it is, depending on conditions, practically possible to detect the types of base contained in a nucleic acid primer bound to the fine particle surface. This point is verified according to the above results.

It is mentioned that a nucleic acid primer binding fine particle is prepared by synthesizing a single strand DNA directly on the fine particle surface by applying the above solid phase sequential synthesis, and the nucleic acid primer thereof includes a single strand DNA having a part of base, deleted therefrom and having a shortened base length. On the other hand, the existence of substantial amount of nucleic acid primers with desired base sequence can be confirmed practically by performing single nucleotide elongation described in Example 2 using a target nucleic acid as template to incorporate a label substance, and assaying dideoxynucleotide having the label substance bound thereto.

Further, different nucleic acid primers can be individually bound to 576 types of fine particles in total mentioned above.

Example 9

Nature Biotechnology Vol. 18, 438, 2000 describes preparation of an oligonucleotide chip for detecting the mutation in exon 7 of the genome DNA of two cell lines HSC4 and HSC5 of human oral squamous carcinoma, and detection of fluorescence labeled nucleic acid derived from the exon.

In this example, ferrite fine particles having oligonucleotide nucleic acid primers bound thereto were used for elongation, and thereby a single nucleotide polymorphism is detected.

A specific procedure thereof is described below.

```
                                              SEQ ID NO: 18
5' HS-(CH2)6-O-PO2-O-GATGGGCCTCCGGTTCA 3'

SEQ ID NO: 19
5' HS-(CH2)6-O-PO2-O-GATGGGCCTCCGGTTCT 3'
```

A single strand nucleic acid of SEQ ID NO: 18, having a base sequence complementary to a part of the base sequence of the above exon 7 of HSC4 (a part containing codon No. 248) and carrying a sulfanil group (—SH) at the 5' end for binding to the fine particle, was synthesized in the same manner as in Example 1. Though SEQ ID NO: 18 is completely complementary, a single strand nucleic acid of SEQ ID NO: 19 was synthesized, which had single base mismatch site (underlined part) to the base sequence of the target nucleic acid.

Among 256 types of ferrite fine particles labeled with the atom group consisting Co, Ni, Mn, Zn, Cu, Mg, Al and Ti, selected were E particle and F particle labeled with "Ni, Mn, Zn, Cu, Mg, Al and Ti" and "Co, Ni, Mn, Zn, Cu, Mg and Al", respectively. In the same manner as in Example 6, maleimide groups were introduced to the surfaces of E and F particles, and single strand nucleic acids of SEQ ID NOS: 18 and 19 were bound to E and F particles, respectively. Regarding the prepared two types of nucleic acid primer-binding ferrite fine particles, the methods described in Example 6 were used to distinguish labels bound to particles and to confirm nucleic acid primers bound to the surface of each particle.

```
                                              SEQ ID NO: 20
E7S:    5'-ACTGGCCTCATCTTGGGCCT-3' (exon 7, sense)

SEQ ID NO: 21
E7A:    5'-TGTGCAGGGTGGCAAGTGGC-3' (exon 7, anti-
                                              sense)
```

Next, an exon 7 portion from the genome of HSC4 was amplified by PCR reaction using PCR nucleic acid primers of the above SEQ ID NOS: 20 and 21 (the synthesis thereof was ordered to Bex Co., Ltd.), by use of a commercially available PCR amplification kit. That is, 50 µl of PCR mixture containing 20 ng of genome DNA, 0.4 µM of sense nucleic acid primer E7S and 0.4 µM of anti-sense nucleic acid primer E7A, was subjected to 40 cycles of PCR amplification, each cycle consisting of 30 seconds at 94° C. and 45 seconds at 60° C. The obtained product was designed to have a chain length of 171 nucleotides.

Next, regarding each of the above two types of nucleic acid primer-binding particles, a proper amount of each nucleic acid primer binding-particle and Br-dUTP as deoxynucleotide triphosphate with labeling substance bound thereto were used for elongation reaction (ssPCR: single strand PCR), using the above amplified product as template, in the same manner as in Example 1.

After the elongation reaction, ferrite fine particles in each reaction solution were properly washed with pure water; collected; and dried under reduced pressure. Thereafter, ions derived from label substance (Br) in deoxynucleotide triphosphate with the label substance bound thereto were observed with a TOF-SIMS apparatus by the above-mentioned method. From E particle, bromine ions ($^{79}Br^-$ and $^{81}Br^-$ ions) derived from the above Br-dUTP, which was introduced by the elongation reaction, were detected, in addition to each atomic ion contained as a label. On the other hand, from F particle, each atomic ion contained as a label was detected, but bromine ions were not detected. That is, the single strand DNA of SEQ ID NO: 19 bound to the surface of F particle had different single nucleotide at its 3' end and thus base pairs with target nucleic acid of template were not formed at the 3' end. This confirms that no elongation reaction to 3' end occurred.

According to these results, it is understood that the nucleic acid primer-binding fine particle of the present invention enables the detection of a single nucleotide polymorphism of a gene derived from actual cell genome as more practical type though it is a model type.

It should be noted that 256 types of ferrite fine particles mentioned in this example can have an arbitrary probe bound thereto and can be used to detect a single nucleotide polymorphism.

Use of the method of labeling an object according to the present invention enables binding of many types of labels, if needed, to a minute object such as a fine particulate substrate to be used for fixing probe molecules to be used in, e.g., bioassay. In other words, fixation of predetermined probe molecules on the surface of a fine particulate substrate to which labels have been bound in advance by applying the method of labeling an object according to the present invention enables easy binding of labels that may be used for distinguishing the types of individual probe molecules to many types of probe molecules fixed on a fine particle. Further, the above bioassay is available using, for example, fine particles that are labeled by the above labeling method.

Use of the nucleic acid primer bound to a labeled object according to the present invention enables the provision of a fine particle fixation type nucleic acid primer molecule, wherein a fine particulate substrate having a nucleic acid primer molecule used in, for example, various bioassay, fixed on the surface thereof, is provided with easily distinguishable various labels, which correspond to the types and base sequence of each nucleic acid primer. In other words, the method used in the present invention permits an extremely large number of types of labels to be bound to fine particulate substrates, which have nuclei acid primer molecules fixed thereon. Fixation of a designated nucleic acid primer on the surface of the labeled fine particle can provide a label available for identifying the types of individual nucleic acid primer molecule to various types of nucleic acid primer molecules of fine particle fixation type. For example, when a large number of types of nucleic acid primer molecules are used for bioassay, each of the nucleic acid primer molecules is fixed to a fine particulate substrate with a label bound thereto and the nucleic acid primer molecule can be specified with no error by identifying the label bound to the fine particulate substrate.

The present invention is not limited to the above embodiments and various changes and modifications can be made within the spirit and scope of the present invention. Therefore to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2005-230597, filed Aug. 9, 2005, and 2005-230598, filed Aug. 9, 2005 which are hereby incorporated by reference herein in their entirety.

What is claimed is:

1. A set of plural particles used for discrimination of a target substance, comprising at least 31 particles,
   wherein each of the plural particles binds on its surface to a biological substance,
   wherein each of the plural particles comprises a label corresponding to the bound biological substance, and
   wherein the plural particles are labeled by at least 31 types of labels discriminated by the existence/non-existence of at least 5 types of atoms.

2. The set of plural particles according to claim 1, wherein the biological substance is a probe.

3. The set of plural particles according to claim 2, wherein the probe is one of a pair of substances selected from nucleic acids, DNAs, RNAs, cDNAs, cRNAs, oligodeoxyribonucleotides, polydeoxyribonucleotides, oligoribonucleotides, polyribonucleotides, peptide nucleic acids (PNAs), oligopeptide nucleic acids, peptides, oligopeptides, polypeptides, proteins, antigens, antibodies, enzymes, ligands, ligand receptors, sugars and sugar chains and capable of being bound with the substances recognizing each other.

4. The set of plural particles according to claim 1, wherein the biological substance is a nucleic acid primer.

5. The set of plural particles according to claim 4, wherein the nucleic acid primer is selected from the group consisting of oligodeoxyribonucleotides, polydeoxyribonucleotides, oligoribonucleotides and polyribonucleotides.

6. The set of plural particles according to claim 5, wherein the nucleic acid primer is bound covalently to the surface of the particle directly or indirectly via a linker at the 5' terminal side of the primer.

7. The set of plural particles according to claim 1, wherein at least one of the plural particles is a magnetic material.

8. The set of plural particles according to claim 1, wherein the at least 5 types of atoms are selected from the group consisting of Ni, Mn, Zn, Cu, Mg, Al and Ti.

9. The set of plural particles according to claim 1, wherein the label is identified by at least one of mass spectrometry, X-ray photoelectron spectroscopy and Auger electron spectroscopy.

10. The set of plural particles according to claim 1, wherein the label is included in the particle.

* * * * *